(12) United States Patent
Jackson et al.

(10) Patent No.: US 11,970,785 B2
(45) Date of Patent: *Apr. 30, 2024

(54) METHODS AND MATERIALS FOR MULTIPLEXED COLLECTIONS OF FUNCTIONAL LIGANDS

(71) Applicant: Base Pair Biotechnologies, Inc., Pearland, TX (US)

(72) Inventors: George W. Jackson, Pearland, TX (US); Robert Batchelor, Pearland, TX (US); Alexander S. Chiu, Pearland, TX (US); Rafal Drabek, Houston, TX (US); Deepak Thirunavukarasu, Houston, TX (US); Caitlin Bruns, Webster, TX (US)

(73) Assignee: BASE PAIR BIOTECHNOLOGIES, INC., Pearland, TX (US)

( * ) Notice: Subject to any disclaimer, the term of this patent is extended or adjusted under 35 U.S.C. 154(b) by 149 days.

This patent is subject to a terminal disclaimer.

(21) Appl. No.: 17/460,513

(22) Filed: Aug. 30, 2021

(65) Prior Publication Data

US 2021/0395920 A1 Dec. 23, 2021

Related U.S. Application Data

(62) Division of application No. 16/262,825, filed on Jan. 30, 2019, now Pat. No. 11,111,603.

(60) Provisional application No. 62/624,063, filed on Jan. 30, 2018.

(51) Int. Cl.
*C07H 21/04* (2006.01)
*C12Q 1/6811* (2018.01)
*C12Q 1/6837* (2018.01)
*C40B 40/06* (2006.01)

(52) U.S. Cl.
CPC ............ *C40B 40/06* (2013.01); *C12Q 1/6811* (2013.01); *C12Q 1/6837* (2013.01)

(58) Field of Classification Search
None
See application file for complete search history.

(56) References Cited

U.S. PATENT DOCUMENTS

2014/0371087 A1* 12/2014 Muraca ................. G16B 25/10
705/2

* cited by examiner

*Primary Examiner* — Kimberly Chong
(74) *Attorney, Agent, or Firm* — Equip LG; Christopher Quan

(57) ABSTRACT

This invention relates to methods and materials for multiplexed utilization of collections of functional ligands, particularly to methods and materials for selecting for and/or utilizing particular desirable traits of functional ligands in a multiplexed manner, and more particularly to methods and materials for selecting for and/or utilizing particular structural changes of functional ligands in a multiplexed manner.

18 Claims, 3 Drawing Sheets

Specification includes a Sequence Listing.

METHODS AND MATERIALS FOR MULTIPLEXED COLLECTIONS OF FUNCTIONAL LIGANDS

CROSS-REFERENCE TO RELATED APPLICATIONS

This application is a divisional of U.S. utility application Ser. No. 16/262,825, filed Jan. 30, 2019, entitled "METHODS AND MATERIALS FOR MULTIPLEXED COLLECTIONS OF FUNCTIONAL LIGANDS", which claims the benefit and priority of U.S. provisional patent application Ser. No. 62/624,063, filed Jan. 30, 2018, entitled "METHODS AND MATERIALS FOR MULTIPLEXED COLLECTIONS OF FUNCTIONAL LIGANDS", the contents of all of which are hereby incorporated by reference in their entireties.

COPYRIGHT NOTICE

A portion of the disclosure of this patent document contains material which is subject to copyright protection. The copyright owner has no objection to the facsimile reproduction by anyone of the patent document or the patent disclosure, as it appears in the U.S. Patent and Trademark Office patent file or records, but otherwise reserves all copyright rights whatsoever.

FIELD OF THE INVENTION

This invention relates to methods and materials for multiplexed utilization of collections of functional ligands, particularly to methods and materials for selecting for and/or utilizing particular desirable traits of functional ligands in a multiplexed manner, and more particularly to methods and materials for selecting for and/or utilizing particular structural changes of functional ligands in a multiplexed manner.

SEQUENCE LISTING

Deoxyribonucleic acid (DNA) sequences, which are disclosed in the ASCII text file entitled "P1011US18_ST25.txt", created on Jan. 30, 2019 and of 78.5 KB in size, which is incorporated by reference in its entirety, herein are intended to include other aptamers incorporating modifications, truncations (e.g. trivial truncations, such as 1-5 nucleotides removed at an end, which consist essentially of the same sequence and retains binding to the target molecule), incorporations into larger molecules or complexes (e.g. the aptamer sequence within a longer nucleic acid strand), and/or other aptamers having substantial structural or sequence homology, for example, greater than 75% sequence homology within a similar length of nucleic acid (e.g. similar to within 5-10 nucleotides in length with significant sequence homology within that length, such as greater than 75%), as well as RNA and/or other non-DNA/RNA aptamers. The disclosed aptamers may also bind to homologous proteins or molecules from organisms other than the organisms listed herein, to recombinant or non-recombinant versions of the proteins or molecules, to modified versions of the proteins or molecules, to proteins or molecules from sources other than the source listed herein. The aptamers are artificial, non-naturally occurring sequences designed and/or selected for specific and/or high affinity binding to a target molecule, such as, without limitation, SEQ ID Nos. 1-69 may generally bind to the target molecule lipoarabinomannan (LAM), SEQ ID Nos. 70-188 may generally bind to the target molecule Tetrakis (hydroxymethyl) phosphonium sulfate (THPS), and SEQ ID Nos. 189-301 may generally bind to the target molecule bronopol. SEQ ID No. 302 and SEQ ID No. 304 may generally be utilized as a leading or priming sequence appended to the 5'-end of any of the aptamer sequences presented herein and SEQ ID No. 303 and SEQ ID No. 305 may generally be utilized as a trailing or priming sequence appended to the 3'-end of any of the aptamer sequences presented herein, or vice versa or any combination thereof.

BACKGROUND OF THE INVENTION

Aptamers, which are nucleic acid ligands capable of binding to molecular targets, have recently attracted increased attention for their potential application in many areas of biology and biotechnology. They may be used as sensors, therapeutic tools, to regulate cellular processes, as well as to guide drugs to their specific cellular target(s). Contrary to the actual genetic material, their specificity and characteristics are not directly determined by their primary sequence, but instead by their secondary and/or tertiary structure. Aptamers have been recently investigated as immobilized capture elements in a microarray format. Others have recently selected aptamers against whole cells and complex biological mixtures. Aptamers may also, for example, exhibit changes in their secondary and/or tertiary structure depending on whether it is complexed or uncomplexed with a target molecule.

Aptamers are commonly identified by an in vitro method of selection sometimes referred to as Systematic Evolution of Ligands by EXponential enrichment or "SELEX". SELEX typically begins with a very large pool of randomized polynucleotides which is generally narrowed to one aptamer ligand per molecular target. Once multiple rounds (typically 10-15) of SELEX are completed, the nucleic acid sequences are identified by conventional cloning and sequencing. Aptamers have most famously been developed as ligands to important proteins, rivaling antibodies in both affinity and specificity, and the first aptamer-based therapeutics are now emerging. More recently, however, aptamers have been also developed to bind small organic molecules and cellular toxins, viruses, and even targets as small as heavy metal ions.

SUMMARY OF THE INVENTION

The present invention relates to methods and materials for multiplexed utilization of collections of functional ligands, particularly to methods and materials for selecting for and/or utilizing particular desirable traits of functional ligands in a multiplexed manner, and more particularly to methods and materials for selecting for and/or utilizing particular structural changes of functional ligands in a multiplexed manner.

In general, functional ligands may be selected for and/or utilized for their ability to bind or complex to particular target molecules, and/or for the manner in which they bind or complex to particular target molecules, such as by exhibiting a detectable structural change. For example, numerous biomolecules, such as nucleic acids and peptides, take on varied secondary and tertiary structures in response to different environments or by associating with other molecules. Functional ligands may generally include biomolecules such as nucleic acids, such as single-stranded nucleic acids and double-stranded nucleic acids or combinations or regions of both, peptides, other biopolymers and/or combinations or modifications thereof, such as artificially modified nucleic acids, synthetic analogs and the like. A collection of these functional ligands may be utilized for various purposes, which may include, but are not limited to, selecting members of the collection for binding activity to particular target molecule(s) which may result in a desired structural change of the binding member(s), utilizing a collection of functional ligands to detect and/or quantify the presence or absence of target molecule(s) in a sample, determining whether members of a collection bind to more than one target molecule or whether binding events are affected by the presence of multiple target molecules, and/or any other appropriate purpose for utilizing such collections. The target molecule(s) may be, for example and without limitation, proteins, cells, small molecules, biomolecules, and/or combinations or portions thereof.

In general, the collection may be present in a spatial arrangement, such as an array, collection of discrete droplets or multiwell plate, or other system where particular locations of functional ligands are known or readily determinable, such as with tagged or labeled beads. For example, the functional ligands may be arrayed in a stable spatial arrangement or they may be tagged or marked in a manner that their particular locations are determinable (discriminating between different functional ligands). Structural changes may be directly observable, such as through microscopy, microscale thermophoresis (MST), backscattering interferometry (BSI), and/or any other appropriate observation method. Structural changes may also be detectable through secondary events, such as by detecting changes in fluorescence or other radiation emissions due to alterations in the structure of a functional ligand.

In one aspect of the present invention, a method for selecting functional ligands may include providing a collection of functional ligands, introducing at least one target molecule and detecting possible binding activity between at least one member of the collection and the at least one target molecule by detecting a structural change in the at least one member. In some embodiments, the functional ligands may bind to or complex with another molecule, which may serve as an indicator, in a manner that is affected by a binding event between the functional ligand and a target molecule. For example, the binding of the functional ligand and the indicator may be disrupted by the binding of a target molecule to the functional ligand, or vice versa. The indicator may also be a part of the functional ligand, such as forming a different region of the functional ligand that may self-associate.

The functional ligand and the indicator may each carry a label or tag that may interact with each other to produce a detectable signal, or interact with each other to reduce a detectable signal. For example, the functional ligand and the indicator may carry a radiation-emitting label and a radiation-quenching or reducing label, respectively, or vice versa. They may also carry a pair of labels that interact via Forster resonance energy transfer (FRET) and/or any other appropriate signal-interaction mechanism.

In general, variations to the binding conditions may also be employed, such as to detect variations in structural changes, binding affinity, cross-reactivity, detection limits, and/or any other appropriate variation. For example variations in binding conditions may include, but are not limited to, concentrations of the target molecules, inclusion of other target molecules, variation in pH, temperature, pressure, flow, electrical gradient, solvent, degree of complementarity between functional ligands and indicators, solute makeup/concentration, spacing of functional ligands, spacing between functional ligands and a substrate, and/or any other appropriate variation in binding conditions.

In some embodiments, the functional ligands included in a collection may be randomized or unknown. In other embodiments, at least one of the functional ligands may be selected previously for a known or suspected trait or characteristic, such as known binding to a particular target molecule, predicted or observed structural changes during binding events, and/or any other known or suspected trait or characteristic. This may be desirable, for example, to efficiently utilize prior data or experimental results to speed up or narrow selection.

In some exemplary embodiments, the functional ligands may include a single-stranded nucleic acid, such as an aptamer, which may hybridize with an indicator single-stranded nucleic acid in a manner that is affected by the presence of a target molecule of the functional ligand. In some embodiments, the indicator nucleic acid or "Signal oligo" may hybridize to a nucleic acid aptamer in the absence of a target molecule and be displaced and/or occluded from hybridizing upon binding of a target molecule to the aptamer. In some embodiments, the Signal oligo and the target molecule may bind to the same region (or part thereof) of the aptamer which may result in competitive binding between them. In other embodiments, the aptamer may adopt a conformational change when it binds to the target molecule, which may, without being bound to any particular theory, result in the occlusion of the Signal oligo or otherwise making the hybridization thermodynamically unfavorable due to the conformation change. The unhybridized Signal oligo and/or aptamer may then be utilized to detect a structural change in the aptamer.

In some embodiments, the detected structural change at a particular spatial location or with a particular determinable location may be utilized to indicate which functional ligand experienced a binding event in order to correlate whether a particular functional ligand binds to a particular target molecule.

In some embodiments, multiple target molecules may be introduced to determine which, if any, of the collection bind to them. For example, a collection of potentially binding functional ligands may be exposed to a target molecule and then a detection may be performed to determine if any of the collection binds. Then another target molecule may be added and a further detection performed and so forth. In general, the known spatial locations of particular functional ligands may be known or determinable for each exposure/binding with a known target molecule such that binding events may be correlated to particular functional ligands and target molecules.

In another aspect of the present invention, a method for utilizing functional ligands may include providing a collection of functional ligands which are known to bind to particular target molecules in a manner that produces a detectable structural change, introducing a sample to such collection and determining whether such sample contains any target molecules of such collection of functional ligands by detecting any structural changes in such functional ligands. In some embodiments, the functional ligands may bind to or complex with another molecule, which may serve as an indicator, in a manner that is affected by a binding event between the functional ligand and a target molecule. For example, the binding of the functional ligand and the indicator may be disrupted by the binding of a target molecule to the functional ligand, or vice versa. The indicator may also be a part of the functional ligand, such as forming a different region of the functional ligand that may self-associate.

In some exemplary embodiments, the functional ligand may include an aptamer, as discussed above, which may associate with a Signal oligo. The unhybridized Signal oligo and/or aptamer may then be utilized to detect a structural change in the aptamer.

In some embodiments, the detected structural change at a particular spatial location or with a particular determinable location may be utilized to indicate which functional ligand experienced a binding event and thus which target molecule(s) are present in the sample.

The degree of detected structural changes may also be utilized to, for example, to determine abundance and/or concentration of a target molecule(s) in the sample.

In some embodiments, functional ligands may be predisposed on an array substrate in a predetermined spatial arrangement. The functional ligands may, for example, be covalently or otherwise attached to the substrate. The indicators, such as the Signal oligos, may also be attached to the substrate rather than the functional ligands to which they bind or hybridize, or both may be attached in a way that they may bind or hybridize and also produce a detectable structural change when exposed to an appropriate target molecule.

In further embodiments, functional ligands and/or the indicators may be synthesized in situ on the array, such as by light directed in situ nucleic acid synthesis.

The members of the collection and/or the indicators may also include detectable portions, such as, for example, fluorescent moieties, radioactive tags and/or other appropriate detectable portions.

In some embodiments, any displaced functional ligands and/or indicators may be collected and/or otherwise subjected to a sequencing and/or compositional analysis, such as to verify which functional ligands, if any, experienced a binding event that resulted in a free functional ligand and/or indicator that may be analyzed.

In further embodiments, a collection of functional ligands may include peptide sequences and contacting the collection with at least one target molecule. In some exemplary embodiments, the peptide sequence may be tagged, linked, marked and/or otherwise associated with a nucleic acid sequence. The nucleic acid sequence may be, for example, representative of the sequence of the peptide. For example, the nucleic acid may substantially encode the peptide sequence. Also for example, the nucleic acid may be a unique or semi-unique identifier sequence. The nucleic acid sequence may then be utilized to bind an indicator, as described above, such that a peptide bound to a target molecule may be correlated by the structural change in the nucleic acid sequence and/or the indicator.

The present invention together with the above and other advantages may best be understood from the following detailed description of the embodiments of the invention and as illustrated in the drawings. The following description, while indicating various embodiments of the invention and numerous specific details thereof, is given by way of illustration and not of limitation. Many substitutions, modifications, additions or rearrangements may be made within the scope of the invention, and the invention includes all such substitutions, modifications, additions or rearrangements.

DETAILED DESCRIPTION OF THE INVENTION

Figure 1:
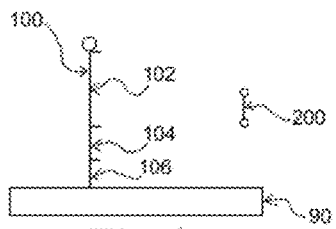
FIGS. 1, 1a, 1b and 1c illustrate an embodiment of a functional ligand attached to a substrate and indicator interacting with the presence of a target molecule to produce a signal.

The detailed description set forth below is intended as a description of the presently exemplified methods, devices, and compositions provided in accordance with aspects of the present invention and is not intended to represent the only forms in which the present invention may be practiced or utilized. It is to be understood, however, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the exemplified methods, devices and materials are now described.

The present invention relates to methods and materials for multiplexed utilization of collections of functional ligands, particularly to methods and materials for selecting for and/or utilizing particular desirable traits of functional ligands in a multiplexed manner, and more particularly to methods and materials for selecting for and/or utilizing particular structural changes of functional ligands in a multiplexed manner.

In general, functional ligands may be selected for and/or utilized for their ability to bind or complex to particular target molecules, and/or for the manner in which they bind or complex to particular target molecules, such as by exhibiting a detectable structural change. For example, numerous biomolecules, such as nucleic acids and peptides, take on varied secondary and tertiary structures in response to different environments or by associating with other molecules. Further in general, functional ligands may generally include any molecule that undergoes large or otherwise detectable conformational or structural changes when particular binding events occur.

Functional ligands may generally include biomolecules such as nucleic acids, such as single-stranded nucleic acids and double-stranded nucleic acids or combinations or regions of both, peptides, other biopolymers and/or combinations or modifications thereof, such as artificially modified nucleic acids, synthetic analogs and the like. Non-naturally occurring sequences of functional ligands, such as nucleic acids and nucleic acid analogs, such as aptamers, may also be useful by interacting with a target molecule in a manner not present in naturally occurring systems or situations, such as by, for example, not being already present or having a pre-existing function in a naturally occurring setting.

Other examples of functional ligands may include, but are not limited to, G-protein receptors, ion channels, promoter or enhancer elements of DNA, nucleic acid beacons/probes which exhibit conformational changes, and/or any other appropriate functional ligands with the desired structural/conformational changing properties.

In general, functional ligands may generally include nucleic acids, particularly single-stranded nucleic acids, peptides, other biopolymers and/or combinations or modifications thereof. Nucleic acid sequences may include naturally-occurring biomolecules such as ribonucleic acid (RNA), deoxyribonucleic acid (DNA), artificially modified nucleic acids, and/or combinations thereof. In general, modified nucleic acid bases may be utilized and may include, but are not limited to, 2'-Deoxy-P-nucleoside-5'-Triphosphate, 2'-Deoxyinosine-5'-Triphosphate, 2'-Deoxypseudouridine-5'-Triphosphate, 2'-Deoxyuridine-5'-Triphosphate, 2'-Deoxyzebularine-5'-Triphosphate, 2-Amino-2'-deoxyadenosine-5'-Triphosphate, 2-Amino-6-chloropurine-2'-deoxyriboside-5'-Triphosphate, 2-Aminopurine-2'-deoxyribose-5'-Triphosphate, 2-Thio-2'-deoxycytidine-5'-Triphosphate, 2-Thiothymidine-5'-Triphosphate, 2'-Deoxy-L-adenosine-5'-Triphosphate, 2'-Deoxy-L-cytidine-5'-Triphosphate, 2'-Deoxy-L-guanosine-5'-Triphosphate, 2'-Deoxy-L-thymidine-5'-Triphosphate, 4-Thiothymidine-5'-Triphosphate, 5-Aminoallyl-2'-deoxycytidine-5'-Triphosphate, 5-Aminoallyl-2'-deoxyuridine-5'-Triphosphate, 5-Bromo-2'-deoxycytidine-5'-Triphosphate, 5-Bromo-2'-deoxyuridine-5'-Triphosphate, 5-Fluoro-2'-deoxyuridine-5'-Triphosphate, 5-Trifluoromethyl-2-deoxyuridine-5'-Triphosphate, and/or any other appropriate modified nucleic acid base. It may generally be understood that the nucleoside triphosphates (NTPs) listed above may generally refer to any appropriate phosphate of the modified base, such as additionally, for example, monophosphates (NMPs) or diphosphates (NDPs) of the base. Embodiments of the SELEX method may generally be utilized to select or preselect for aptamers to be used in a collection. The basic SELEX protocol and aptamers are described in U.S. Pat. No. 5,270,163, entitled "Methods for identifying nucleic acid ligands," the entire contents of which are hereby incorporated by reference.

A collection of these functional ligands may be utilized for various purposes, which may include, but are not limited to, selecting members of the collection for binding activity to particular target molecule(s) which may result in a desired structural change of the binding member(s), utilizing a collection of functional ligands to detect and/or quantify the presence or absence of target molecule(s) in a sample, determining whether members of a collection bind to more than one target molecule or whether binding events are affected by the presence of multiple target molecules, and/or any other appropriate purpose for utilizing such collections. The target molecule(s) may be, for example and without limitation, proteins, cells, small molecules, biomolecules, and/or combinations or portions thereof.

In general, the collection may be present in a spatial arrangement, such as an array (e.g. microarrays, microfluidic chips (i.e. microchips), handspotted arrays, etc.), collection of discrete droplets or multiwell plate, or other system where particular locations of functional ligands are known or readily determinable, such as with tagged or labeled beads. For example, the functional ligands may be arrayed in a stable spatial arrangement or they may be tagged or marked in a manner that their particular locations are determinable (discriminating between different functional ligands). In other examples, the functional ligands may be attached to beads or other movable substrates which may then be disposed in known locations or spatially organized in a manner where different sets of beads/movable substrates may be kept separated for sorting, selective manipulation and/or prevention of cross-talk/interference from neighboring beads/movable substrates. For example, the beads/movable substrates may be present in separate wells of multiwell plates or in separate discrete droplets.

In embodiments utilizing an array with a solid substrate, the substrates used may be glass, ceramic, metal or polymeric, and/or any other appropriate material. In general, it may be desirable to utilize a material that is convenient for attaching functional ligands and/or for in situ synthesis. Polymers may include synthetic polymers as well as purified biological polymers. The substrate may also be any film, which may be non-porous or macroporous.

The substrate may be generally planar and may be of any appropriate geometry such as, for example, rectangular, square, circular, elliptical, triangular, other polygonal shape, irregular and/or any other appropriate geometry. The substrate may also be of other forms, such as cylindrical, spherical, irregular and/or any other appropriate form.

Appropriate ceramics or metals may include, for example, hydroxyapatite, alumina, graphite, graphene, buckyballs, silica, gold, silver, and pyrolytic carbon.

Appropriate synthetic materials may include polymers such as polyamides (e.g., nylon), polyesters, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, ethylene vinyl acetates, polysulfones, nitrocelluloses and similar copolymers. These synthetic polymers may be woven or knitted into a mesh to form a matrix or similar structure. Alternatively, the synthetic polymer materials can be molded or cast into appropriate forms.

Biological polymers may be naturally occurring or produced in vitro by fermentation and the like or by recombinant genetic engineering. Recombinant DNA technology can be used to engineer virtually any polypeptide sequence and then amplify and express the protein in either bacterial or mammalian cells. Purified biological polymers can be appropriately formed into a substrate by techniques such as weaving, knitting, casting, molding, extrusion, cellular alignment and magnetic alignment. Suitable biological polymers include, without limitation, collagen, elastin, silk, keratin, gelatin, polyamino acids, polysaccharides (e.g., cellulose and starch) and copolymers thereof.

Any suitable substrate may be susceptible to adhesion, attachment or adsorption by functional ligands or indicators, as appropriate. The susceptibility may be inherent or modified. In one example, the surfaces of substrates may be susceptible to adhesion, attachment or adsorption to nucleic acids or peptides/proteins. In another example, the surfaces of substrates may be susceptible to adhesion, attachment or adsorption to proteins or peptides and not to nucleic acids, or vice versa.

In one exemplary embodiment, a glass substrate may have a layer or coating of a material that promotes adhesion with targets, such as proteins, peptides or nucleic acids, materials that maybe charged, such as those that are positively charged, for binding target materials. Examples of charged materials include cellulosic materials, for example, nitrocelluluose, methylcelluose, ethylcellulose, carboxymethyl cellulose, hydroxyethyl cellulose, methylhydroxypropyl cellulose; epoxies, PVDF (polyvinylidene fluoride); partially or fully hydrolyzed poly(vinyl alcohol); poly(vinylpyrrolidone); poly(ethyloxazoline); poly(ethylene oxide)-co-poly (propylene oxide) block copolymers; polyamines; polyacrylamide; hydroxypropylmethacrylate; polysucrose; hyaluronic acid; alginate; chitosan; dextran; gelatin and mixtures and copolymers thereof.

In other embodiments, if the substrate is not susceptible for attachment by charged materials, or may be susceptible only for attachment by wrongly charged materials, some areas of the substrate may have adhesives, binding agents, or similar attached, adsorbed or coated thereon. Examples of adhesives may include any suitable adhesives that bind the charged materials.

The functional ligands may be present on the substrate discretely or in clusters. The distance between the discrete functional ligands may be close or may be far apart and may usually be of different functional ligands. Clusters may be used for multiple spots of a single functional ligand. In general, the distance between placements may be chosen to aid in preventing direct interactions between adjacent functional ligands, to aid in preventing unwanted multiple binding events between a target molecule and adjacent functional ligands, to aid in preventing interference of a binding event due to proximity to an adjacent functional ligand and/or in preventing any other applicable unwanted interactions.

In one embodiment, the substrate may be macroporous. Macroporous substrates may be desirable, for example, if the different functional ligands are very close together. Closely packed functional ligands may, for example, increase the efficiency of the utilization of a particular substrate. A macroporous substrate may be suited for balancing between efficiency and separation. For a macroporous substrate, the walls of the pores may be sufficient to separate even closely packed functional ligands if the pores are large enough to enable the binding process to occur within the pores.

Also, for macroporous substrates, the pores may have an average diameter greater than the average size of the target molecule(s) such that they may enter or partly enter the pores for binding events to occur. Hydrogels may also be useful for binding or anchoring functional ligands to the pores. Hydrogels may also fill the pores under fluid conditions and present a smooth surface for fluid flow while at the same time may keep the fluid from flowing through the pores.

The plurality of functional ligands may be arranged in any appropriate manner such as, for example, in circular or elliptical spots, square or rectangular spots, stripes, concentric rings and/or any other appropriate arrangement on the subject.

In some embodiments, the functional ligands may also be disposed on beads or other free-floating substrates. For example, glass beads, agarose or cellulosic beads (e.g. Sepharose™ or Sephadex™) nanomaterials, nanoparticles and/or any other appropriate free floating substrate may be utilized. The beads or free-floating substrates may also generally be labeled or tagged such that the identity of the functional ligands attached to them are determinable by identifying the label or tag. For example, fluorescently coded labels (such as color combination fluors) may be utilized to barcode or otherwise uniquely/semi-uniquely identify particular bead(s).

Biotin may also be included on functional ligands or indicator molecules to allow them to be attached to a substrate, such as substrates coated with streptavidin or similar molecules.

Structural changes may be directly observable, such as through microscopy, microscale thermophoresis (MST), backscattering interferometry (BSI), and/or any other appropriate observation method. Structural changes may also be detectable through secondary events, such as by detecting changes in fluorescence or other radiation emissions due to alterations in the structure of a functional ligand.

Pairs of corresponding chromophores and/or fluorophores may be utilized for their ability of altering the conversion efficiency of the radiation converting chromophore and/or fluorophores. For example, converting and absorbing chromophore and/or fluorophores pairs in the radiation portion of interest may include, but are not limited to: ALEXA633™/QSY21™, CY5™/QSY21™, ALEXA647™/QSY21™ ALEXA647™/ALEXA680™, ALEXA680™/allophycocyanin (APC), ALEXA700™/APC, CY3™/BHQ-2, and/or ALEXA750™/APC (Molecular Probes, Inc.), and/or any other appropriate chromophore and/or fluorophores pair. It is contemplated, however, that any suitable pair of first and/or second radiation converting chromophore and/or fluorophore and radiation absorbing chromophore and/or fluorophore, whether now known or later developed, is within the scope of the present invention.

A chromophore-quencher pair may also include a metallic quenching element, such as a gold or other metallic substrate.

In one aspect of the present invention, a method for selecting functional ligands may include providing a collection of functional ligands, introducing at least one target molecule and detecting possible binding activity between at least one member of the collection and the at least one target molecule by detecting a structural change in the at least one member. In some embodiments, the functional ligands may bind to or complex with another molecule, which may serve as an indicator, in a manner that is affected by a binding event between the functional ligand and a target molecule. For example, the binding of the functional ligand and the indicator may be disrupted by the binding of a target molecule to the functional ligand, or vice versa.

Not all binding events may necessarily result in structural or conformational changes which may be detected. Thus, these methods may be utilized to distinguish between structural/conformational switching functional ligands and binding functional ligands which do not undergo such switching behavior. In some situations, structural/conformational switching functional ligands may be more preferable or desirable to use in particular applications as opposed to functional ligands which do not undergo structural/conformational switching, such as where the structural/conformational switching is more easily detected or quantified as opposed to non-switching binding events. Additionally, some switching events may enable or aid in "one step" detection methods, such as for example with radiation emitting methods as described below, rather than binding events which do not exhibit switching behavior which may require additional steps to detect binding.

Figure 1A:
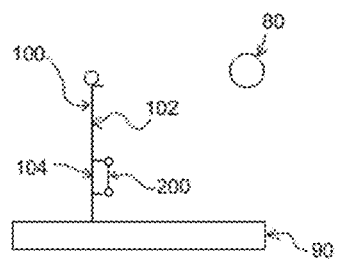

FIG. 1 illustrates an example of a functional ligand 100 and an indicator 200, shown with the functional ligand 100 attached to a substrate 90. The functional ligand 100 may generally include a target molecule binding region 102, an indicator binding region 104 and/or a linker region 106, where the linker region 106 may serve to space the rest of the functional ligand 100 from the substrate 90 such that it may interact freely with other parts of the system, such as a target molecule 80 and/or the indicator 200. The target molecule binding region 102 and the indicator binding region 104 may also be, for example, overlapping to some degree, spaced apart by another region, one contained within the other and/or any other desirable arrangement. As illustrated in FIG. 1A, indicator 200 may generally bind to the indicator binding region 104, such as by hybridization or other reversible binding. In general, the indicator 200 may bind specifically to an indicator binding region 104 of one species of functional ligand 100 within a collection, or it may bind to multiple or all of the members of a collection in a non-specific manner. A non-specific indicator 200 may be desirable for ease and/or cost savings for producing the indicators, as well as for consistency in designing of the functional ligands 100.

Figure 1B:
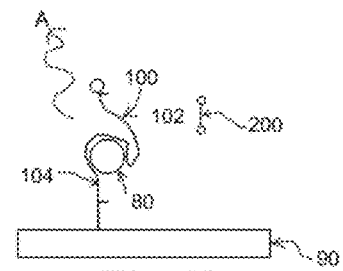

In the presence of a target molecule 80 which binds to the functional ligand 100, the functional ligand 100 may generally adopt a conformation which binds to the target molecule 80, as illustrated in FIG. 1B. In cases where the structural change of the functional ligand 100 is significant, the conformational change may generally result in the indicator 200 being displaced and/or otherwise unable to remain bound to the functional ligand 100, as illustrated in FIG. 1B. This may generally be detected as a signal or observable event A.

Figure 2:
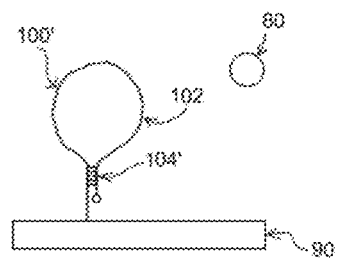
FIGS. 2, 2a, 2b and 2c illustrate embodiments of a functional ligand attached to a substrate interacting with the presence of a target molecule to produce a signal.

The indicator may also be a part of the functional ligand, such as forming a different region of the functional ligand that may self-associate. FIG. 2 illustrates an example of a functional ligand 100' which self-binds or self-hybridizes at zone 104' which may be disrupted to produce a signal or observable event A when the functional ligand 100' binds a target molecule 80, as shown in FIG. 2A.

The functional ligand and the indicator may each carry a label or tag that may interact with each other to produce a detectable signal, or interact with each other to reduce a detectable signal. For example, the functional ligand and the indicator may carry a radiation-emitting label and a radiation-quenching or reducing label, respectively, or vice versa. They may also carry a pair of labels that interact via Forster resonance energy transfer (FRET) and/or any other appropriate signal-interaction mechanism.

Figure 1C:
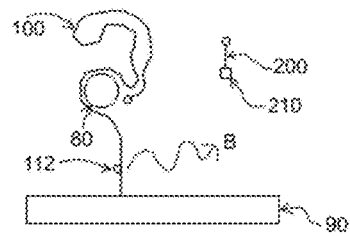

FIG. 1C illustrates the example shown in FIGS. 1, 1A and 1B where the functional ligand 100 and the indicator 200 carry a signal interacting pair, such as a signal emitting label 112 and a signal attenuating label 210, respectively, such that when the functional ligand 100 and the indicator 200 are bound, the labels 112, 210 interact due to proximity resulting in the signal B from label 112 being attenuated or quenched. The binding of the target molecule 80 and the subsequent increase in distance between the labels 112, 210 may then result in the emission of a signal B from the label 112 which may be detected.

Figure 2A:
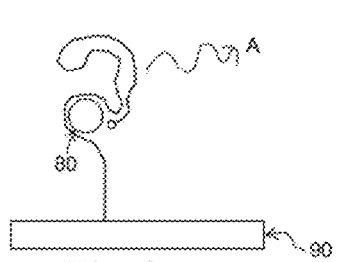
Figure 2B:
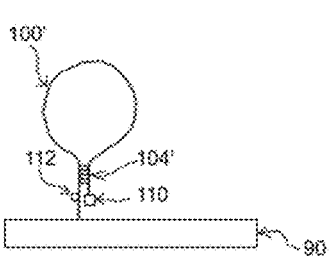
Figure 2C:
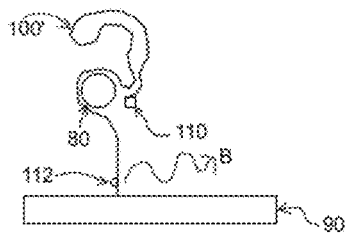

FIGS. 2B and 2C illustrate the example shown in FIGS. 2 and 2A where the functional ligand 100' carries a signal emitting label 112 and a signal attenuating label 110 at different positions of the functional ligand 100' such that when the self-interaction 104' occurs, the labels 112, 110 interact due to proximity resulting in the signal B from label 112 being attenuated or quenched, or vice versa. The binding of the target molecule 80 and the subsequent increase in distance between the labels 112, 110 may then result in the emission of a signal B from the label 112 (or 110 as appropriate) which may be detected.

Figure 6:
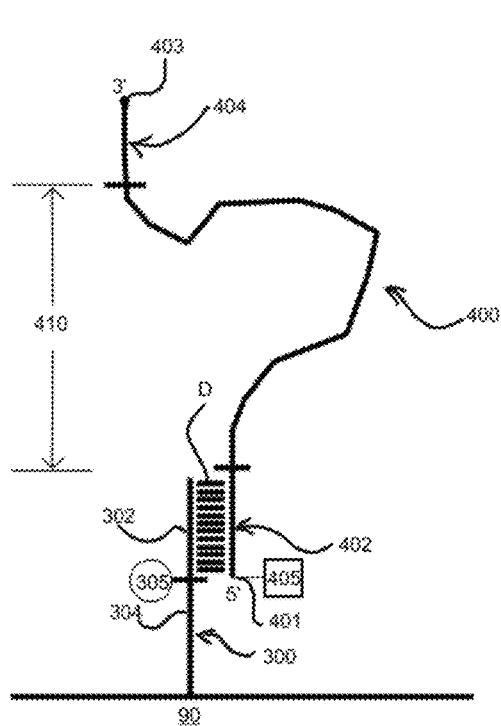
FIGS. 6 and 6a illustrates an embodiment of a functional ligand and an indicator attached to a substrate with a spacing region interacting with the presence of a target molecule to produce a signal.
Figure 6A:
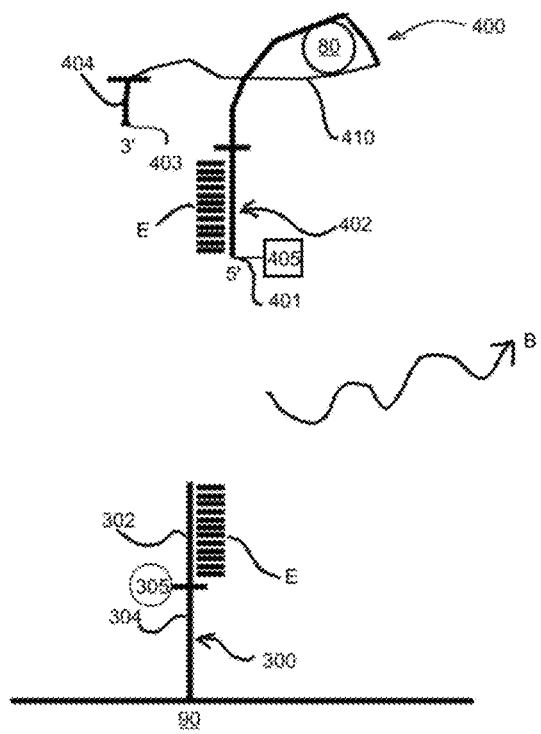

FIGS. 6 and 6a illustrate an example where a functional ligand 400 and an indicator 300 carry a signal interacting pair, such as a signal emitting label 405 and a signal attenuating label 305, respectively (or vice versa), such that when the functional ligand 400 and the indicator 300 are bound, such as through hybridization D of complementary or partially complementary regions 302, 402, the labels 305, 405 interact due to proximity resulting in the signal B from label 405 (or 305 if reversed) being attenuated or quenched. The binding of the target molecule 80 to the binding region 410 of the functional ligand 400, as illustrated in FIG. 6a, may generally cause a conformational change in the functional ligand 400 which may generally result in the complementary or partially complementary regions 302, 402 dehybridizing E to release the functional ligand 400 from the indicator 300 and the subsequent increase in distance between the labels 305, 405 may then result in the emission of a signal B which may be detected. The labels 305, 405 may be attached to or integrated into the functional ligand 400 and the indicator 300, such as by covalent attachment, within the strand of the molecule, such as in the middle (as illustrated with label 305 in the middle of indicator 300) or at a terminal end (e.g. the 5' end 401 as illustrated or the 3' end 403 if the region 404 is designed to hybridize with the region 302). Other attachment methods may include but are not limited to, non-covalent bonding, streptavidin-biotin coupling and/or any other appropriate method.

In general, the functional ligands and indicators may also be utilized in solution or otherwise suspending a fluid without an attachment to a substrate. To aid in separating the labels from the functional ligands and indicators that have dehybridized due to target, separation techniques may be utilized, such as separating based on size, mass, charge, or other differing characteristics between the functional ligands and indicators. One of the functional ligands or the indicators may also be attached to a feature which aids in separation, such as a magnetic bead or other appropriate feature or substrate, such that one of the functional ligands or the indicators (when unhybridized) may be pulled away from the other, such as by applying a magnetic field and/or washing away the non-magnetically attached molecules. In general, it may be desirable to aid in separating the unhybridized functional ligands and indicators such there may be appropriate distance between their labels to produce detectable signal.

In general, variations to the binding conditions may also be employed, such as to detect variations in structural changes, binding affinity, cross-reactivity, detection limits, and/or any other appropriate variation. For example variations in binding conditions may include, but are not limited to, concentrations of the target molecules, inclusion of other target molecules, variation in pH, temperature, pressure, flow, electrical gradient, solvent, degree of complementarity between functional ligands and indicators, solute makeup/concentration, spacing of functional ligands, spacing between functional ligands and a substrate, and/or any other appropriate variation in binding conditions.

In some embodiments, as illustrated in FIGS. 6 and 6a, a spacing region may be provided between the substrate and a label on the indicator, as shown with spacing region 304 providing a gap between the substrate 90 and the label 305. This may be desirable, for example, to space the label 305 away from the substrate 90 to aid in preventing interactions between the label 305 and the substrate 90 or the molecular coupling between the substrate 90 and the indicator 300 which may, for example and without being bound to any particular theory, cause adverse effects on the signal emission of label 305. The spacing region may also, for example and without being bound to any particular theory, space the region 302 away from the substrate 90 to aid in preventing interactions between the substrate 90 and the region 302 which may interfere with proper hybridization D between the regions 302, 402. In general, the spacing region may be of any appropriate length, such as at least 5 nucleotides in length and generally up to about 20 nucleotides in length.

In some embodiments, the functional ligands included in a collection may be randomized or unknown. In other embodiments, at least one of the functional ligands may be selected previously for a known or suspected trait or characteristic, such as known binding to a particular target molecule, predicted or observed structural changes during binding events, and/or any other known or suspected trait or characteristic. This may be desirable, for example, to efficiently utilize prior data or experimental results to speed up or narrow selection.

In some exemplary embodiments, the functional ligands may include a single-stranded nucleic acid, such as an aptamer, which may hybridize with an indicator single-stranded nucleic acid in a manner that is affected by the presence of a target molecule of the functional ligand. In some embodiments, the indicator nucleic acid or "Signal oligo" may hybridize to a nucleic acid aptamer in the absence of a target molecule and be displaced and/or occluded from hybridizing upon binding of a target molecule to the aptamer. In some embodiments, the Signal oligo and the target molecule may bind to the same region (or part thereof) of the aptamer which may result in competitive binding between them. In other embodiments, the aptamer may adopt a conformational change when it binds to the target molecule, which may, without being bound to any particular theory, result in the occlusion of the Signal oligo or otherwise making the hybridization thermodynamically unfavorable due to the conformation change. The unhybridized Signal oligo and/or aptamer may then be utilized to detect a structural change in the aptamer.

In general, the Signal oligo may be of sufficient length and complementarity to hybridize to the aptamer serving as a functional ligand. The length and complementarity (e.g. hybridization mismatches) may also be varied or modified to alter the melting temperature (Tm) of the hybridization and thus the relative strength of the hybridization. This may be desirable to tune the degree of structural change of the aptamer necessary to cause dehybridization of the Signal oligo, which may thus be utilized in tuning the affinity of the aptamer:target molecule interactions that are detected. In general, the Signal oligo may be approximately 6 nucleotides long or longer, and/or any appropriate length that may effectively hybridize at the temperature and/or other environmental conditions present in the system, as shorter lengths may not provide a sufficiently favorable thermodynamic hybridization.

In some embodiments, the detected structural change at a particular spatial location or with a particular determinable location may be utilized to indicate which functional ligand experienced a binding event in order to correlate whether a particular functional ligand binds to a particular target molecule.

In some embodiments, multiple target molecules may be introduced to determine which, if any, of the collection bind to them. For example, a collection of potentially binding functional ligands may be exposed to a target molecule and then a detection may be performed to determine if any of the collection binds. Then another target molecule may be added and a further detection performed and so forth. In general, the known spatial locations of particular functional ligands may be known or determinable for each exposure/binding with a known target molecule such that binding events may be correlated to particular functional ligands and target molecules.

In further embodiments, functional ligands and/or the indicators may be synthesized in situ on the array, such as by light directed in situ nucleic acid synthesis or by printing peptide or protein expressing genes onto a surface and using cell-free peptide/protein expression and capture to synthesize peptides/proteins at predetermined locations on a surface. This may be desirable to control the position of each functional ligand and/or indicator.

Presynthesized functional ligands and/or indicators may also be attached to predetermined locations on an array, such as with ligation reactions and/or any other appropriate method.

In some embodiments, the functional ligands and/or the indicators may also be placed into discrete fluid droplets or masses and disposed on a surface or array in a predetermined manner. For example, discrete fluid droplets may be generated with one or a combination of functional ligands in each and placed or sputtered onto a surface, such as with the Raindance RainDrop™ technology, where the droplets are immiscible in a carrier fluid and thus are able to be kept separate and sorted/handled without the materials in each droplet interacting. In another example, fiber optic arrays may be utilized with a well formed on the end of each fiber in a fiber optic bundle, thus enabling each individual well to be localized by its carrier fiber and individually interrogated with light. For example, functional ligands and/or the indicators may be present on beads or other small substrates which may be suspended within the droplets. FIG. 4a illustrates an example of formation of discrete droplets where a stream 60 containing functional ligands and/or indicators may be carried in a bulk fluid stream 70 which flows D past an interface 50 where streams of bulk fluid stream 70 exert a pinching C in a pulsing fashion on the stream 60 to create individual droplets 62.

In another aspect of the present invention, a method for utilizing functional ligands may include providing a collection of functional ligands which are known to bind to particular target molecules in a manner that produces a detectable structural change, introducing a sample to such collection and determining whether such sample contains any target molecules of such collection of functional ligands by detecting any structural changes in such functional ligands. In some embodiments, the functional ligands may bind to or complex with another molecule, which may serve as an indicator, in a manner that is affected by a binding event between the functional ligand and a target molecule. For example, the binding of the functional ligand and the indicator may be disrupted by the binding of a target molecule to the functional ligand, or vice versa. The indicator may also be a part of the functional ligand, such as forming a different region of the functional ligand that may self-associate.

In some exemplary embodiments, the functional ligand may include an aptamer, as discussed above, which may associate with a Signal oligo. The unhybridized Signal oligo and/or aptamer may then be utilized to detect a structural change in the aptamer.

In some embodiments, the detected structural change at a particular spatial location or with a particular determinable location may be utilized to indicate which functional ligand experienced a binding event and thus which target molecule(s) are present in the sample.

The degree of detected structural changes may also be utilized to, for example, to determine abundance and/or concentration of a target molecule(s) in the sample.

In some embodiments, functional ligands may be predisposed on an array substrate in a predetermined spatial arrangement. The functional ligands may, for example, be covalently or otherwise attached to the substrate. The indicators, such as the Signal oligos, may also be attached to the substrate rather than the functional ligands to which they bind or hybridize, or both may be attached in a way that they may bind or hybridize and also produce a detectable structural change when exposed to an appropriate target molecule.

Figure 3:
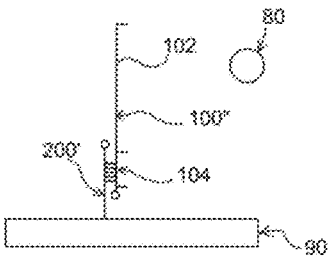
FIGS. 3, 3a and 3b illustrates an embodiment of a functional ligand and an indicator attached to a substrate interacting with the presence of a target molecule to produce a signal.
Figure 3A:
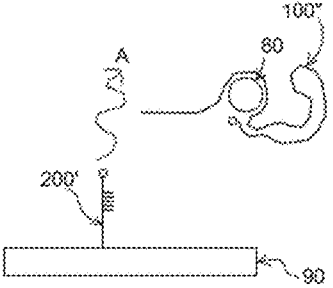
Figure 3B:
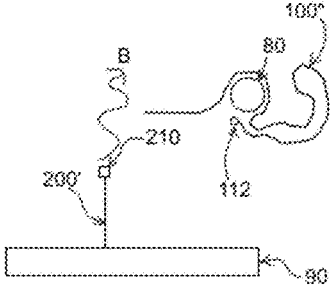

FIG. 3 illustrates an example where the indicator 200' is attached to the substrate 90 and bound or hybridized to the functional ligand 100" via indicator binding region 104. In the presence of a target molecule 80, the functional ligand 100" may then unbind or dehybridize from the indicator 200" to bind to the target molecule 80, such that an observable signal or event A occurs, as shown in FIG. 3A, or in the case with a pair of interacting labels 112, 210, the production of an observable or detectable signal B, as shown in FIG. 3B.

The members of the collection and/or the indicators may also include detectable portions, such as, for example, moieties or portions which participate in detectable interactions or which produce detectable signals, such as colorimetric interactions, refractive index changes, fluorescence interactions (e.g. Fluorescence Energy Transfer (FRET)), fluorescence enhancement upon moving to a different solvent environment, redox interactions, enzymatic interactions, pH reporting mechanisms, surface enhanced Raman scattering (SERS), isothermal DNA amplification, thermal or temperature changes, and/or any other appropriate detectable interactions or signals.

In some embodiments, any displaced functional ligands and/or indicators may be collected and/or otherwise subjected to a sequencing and/or compositional analysis, such as to verify which functional ligands, if any, experienced a binding event that resulted in a free functional ligand and/or indicator that may be analyzed. For example, unhybridized or unbound functional ligands or indicators, as appropriate, may be washed from the collection and sequenced or analyzed, such as by mass spectrometry or other methods, to determine which functional ligands experienced a binding event that resulted in the dehybridization or unbinding. In general, it may be desirable that the indicators, if utilized in this manner, be unique or semi-unique to a respective functional ligand to aid in correlation. In general, aside from standard sequencing methods, parallel sequencing methods, such as, for example, massively parallel sequencing such as 454 Clonal Sequencing (Roche, Branford, CT), massively parallel clonal array sequencing, Solexa Sequencing (Illumina, San Diego, CA), and/or any other appropriate sequencing method may be employed.

In some embodiments, the indicator, such as a Signal oligo, may serve as a primer in a nucleic acid amplification reaction, which may be performed following contacting a collection of functional ligands with target molecule(s). This may be utilized to create amplification products by extension of the indicator primers that are still hybridized and not displaced, which may be detected, such as by addition of nucleic acid-binding dyes or probes.

In further embodiments, a collection of functional ligands may include peptide sequences and contacting the collection with at least one target molecule. Examples of peptide or protein functional ligands may include, but are not limited to, G protein receptors, ion channels, antibodies, peptide aptamers, phage-displayed peptides, and mRNA-displayed peptides. In some exemplary embodiments, the peptide sequence may be tagged, linked, marked and/or otherwise associated with a nucleic acid sequence. The nucleic acid sequence may be, for example, representative of the sequence of the peptide. For example, the nucleic acid may substantially encode the peptide sequence. Also for example, the nucleic acid may be a unique or semi-unique identifier sequence. The nucleic acid sequence may then be utilized to bind an indicator, as described above, such that a peptide bound to a target molecule may be correlated by the structural change in the nucleic acid sequence and/or the indicator.

In some embodiments, methods of incorporating and/or linking nucleic acids to peptides may be utilized, such as, for example, phage display, mRNA display, ribosome display, and/or any other appropriate method. In general, in phage display, a bacteriophage (phage) may be generated that includes a peptide sequence of interest in its protein coat. The phage may further include a nucleic acid sequence that may be representative of the peptide sequence within the nucleic acid of the phage. The phage may then be contacted with target molecules. In general, in mRNA display, a fusion product of a messenger RNA (mRNA) may be linked to a peptide that the mRNA encodes, such as with a puromycin-ended mRNA which may generally cause fusion of the mRNA to the nascent peptide in a ribosome, which may then be contacted with target molecules. Also in general, in ribosome display, a fusion product of a modified mRNA may be utilized that codes for a peptide, but lacks a stop codon and may also incorporate a spacer sequence which may occupy the channel of the ribosome during translation and allow the peptide assembled at the ribosome to fold, which may result in the peptide attached to the ribosome and also attached to the mRNA. This product may then be contacted with target molecules. Other methods may include, but are not limited to, yeast display, bacterial display, and/or any other appropriate method.

Example of Multiplexed Selection of Aptamers with an Array

Figure 4:
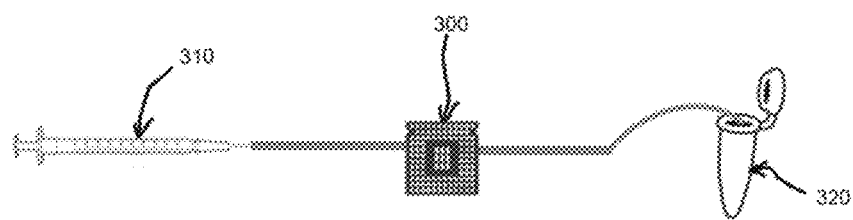
FIG. 4 illustrates a layout of a microfluidic chip with a pump and a collection vessel.
Figure 4A:
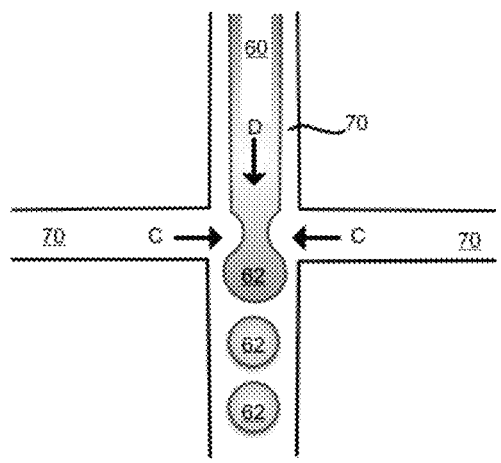
FIG. 4a illustrates the generation of discrete droplets containing functional ligands.
Figure 5:
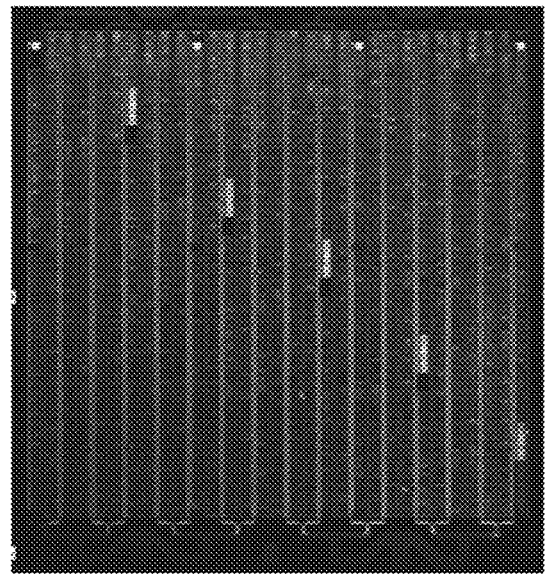
FIG. 5 shows an imaging capture from a microfluidic chip showing fluorescence from particular locations due to target molecule binding.

In an example of a selection protocol with an array, a microarray chip with spatially organized spottings of functional ligands attached to the surface of the chip (aptamer candidates with the sequences SEQ ID Nos. 1-69 with 5' leading sequence SEQ ID No. 302 and 3' ending sequence SEQ ID No. 303), where the identity (e.g. sequence or other identifying information) of the functional ligands at each spot is known, is used in conjunction with a fluidic delivery system, such as a syringe or pump, as illustrated in FIG. 4 with the microfluidic chip 300 with syringe pump 310 and a collection tube 320 for capturing fluid that passes through the microfluidic chip 300. The example functional ligands were selected to potential binding activity to a target molecule, lipoarabinomannan (LAM), a glycolipid, and a virulence factor associated with *Mycobacterium tuberculosi*. The functional ligands were then attached to indicators, such as a Signal oligo which would be hybridized to a nucleic acid aptamer functional ligand, in a buffer or other solution to promote binding (e.g. 1 mM $MgCl_2$, 0.05% Tween-20, 1×PBS pH 7.4 for hybridizing a Signal oligo to an aptamer), such as for approximately 30 minutes. In an example, the aptamer candidates and the Signal oligos may be designed with a corresponding signal-interacting pair (e.g. a fluorophore and quencher pair or other pair as described above) such that upon hybridization, a baseline signal is generated (e.g. quenched fluorescence due to proximity). Signal oligos were designed to be approximately 7 bp in length and complementary to a corresponding portion of the aptamer candidates with a quencher (e.g. 5' Iowa Black RQ dark quencher). The background signal of the microchip was measured to provide a baseline signal measurement. The microchip was washed to remove excess Signal oligos with a buffer. LAM target contained in a buffer at 10 nM concentration was introduced to the microchip and binding was allowed to occur for 30 minutes, after which the microchip was imaged with a GenePix 4000B at 532 nm. The binding process was repeated with increasing concentrations of target (e.g. 50 nM and 250 nM). FIG. 5 illustrates an example imaging of the microchip array, with the brightness of the spots correlating to increased signal detected. Without being bound to any particular theory, the increased signal is taken as correlating to greater conformational changing of the aptamer candidate due to dehybridization of the Signal oligo. SEQ ID Nos. 31, 34, 35, 39, 41, 48 and 53 were identified from signal emitting spots on the microchip and determined to possess binding activity in the approximately 500 pM affinity range to LAM.

Figure 7:
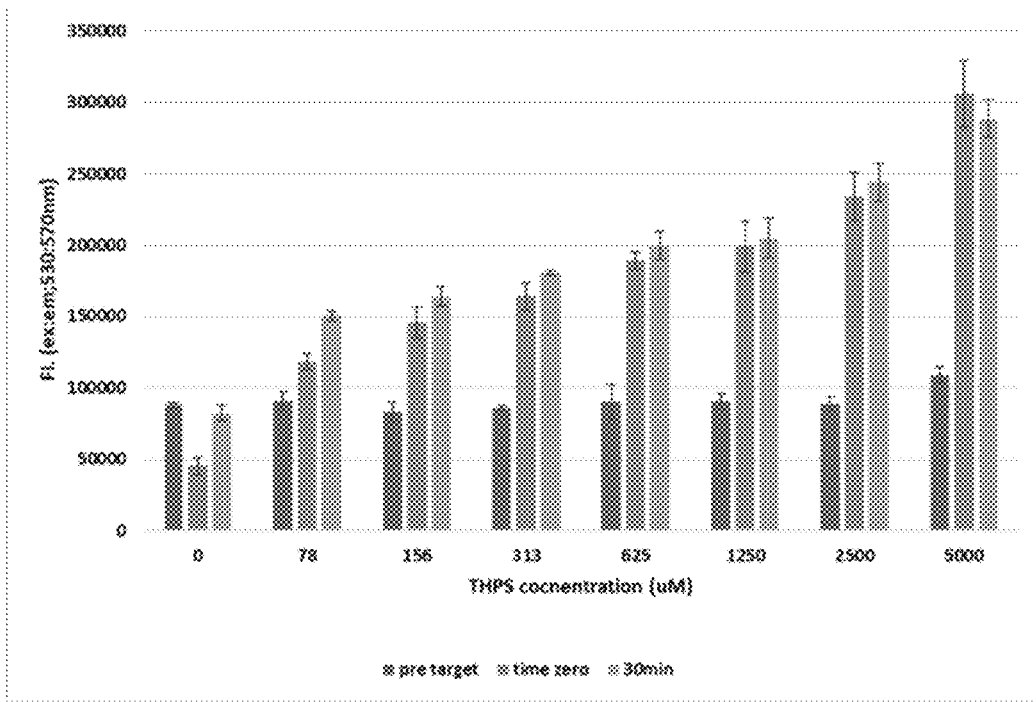
FIG. 7 shows the fluorescence emissions from an example of the embodiment in FIGS. 6 and 6 a with target molecule THPS with the left bar showing pre-target, the middle bar showing time zero and the right bar showing at 30 minutes at each concentration shown.

Example of Detection of Signal from Addition of Target (THPS) to Structure-Switching Aptamers and Indicators In an example of detecting signal from structure switching aptamers and indicators when incubated with the target molecule of the aptamer, a substrate coated with streptavidin was provided with indicator molecules attached via biotin and including a spacing region of between 5 and 20 nucleotides and then hybridized to an aptamer, as illustrated in FIG. 6 with indicator 300 (single-stranded DNA) attached to substrate 90 with spacing region 304 and the aptamer 400 (single-stranded DNA) hybridized D to it via regions 302, 402. The aptamer 400 was provided with a signal emitting label, as shown with label 405 (e.g. Cy3™ dye) attached at the 5'-end of the aptamer 400. The indicator 300 was provided with a signal interacting label 305 (e.g. BHQ-2 quencher), such that when hybridized, the signal interacting label 305 quenches emission of signal from the label 405 when exposed to excitation (e.g. 530 nm light). Progressive concentrations of target molecule 80 were then added to generate conformational change in the aptamer 400 (which was preselected as an aptamer binding to THPS from SEQ ID Nos. 70-188 flanked at its 5'-end with SEQ ID No. 304 and at its 3'-end with SEQ ID 305) to cause dehybridization or otherwise spacing from the indicator 300 to decrease quenching and increase emitted signal due to excitation from the signal emitting label 405. FIG. 7 illustrates the fluorescence detected (shown at 570 nm from a 530 nm excitation source) before addition of target (left bar), at the time of adding target (middle bar) and after 30 minutes of incubation with target (right bar). As illustrated, a concentration-dependent increase in fluorescence was observed with increasing concentrations of target (from 0 to 5000 µM THPS).

Figure 8:
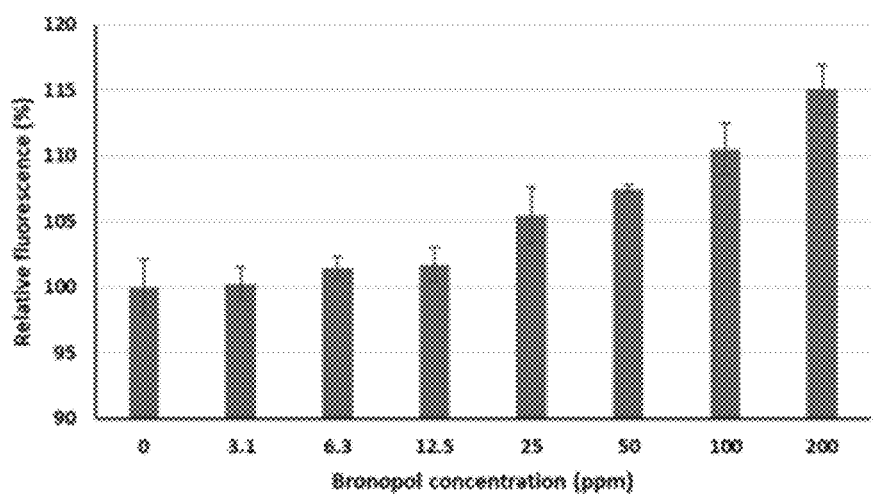
FIG. 8 shows the fluorescence emissions from an example with the target molecule bronopol.

Example of Detection of Signal from Addition of Target (Bronopol) to Structure-Switching Aptamers and Indicators In an example of detecting signal from structure switching aptamers and indicators when incubated with the target molecule of the aptamer, a substrate with an attached aptamer. The aptamer was provided with a signal emitting label as a fluorescent dye covalently attached to the aptamer. An indicator was provided with a signal interacting label as a quencher, such that when hybridized, the signal interacting label on the indicator quenches emission of signal from the label on the aptamer when exposed to excitation (e.g. 530 nm light). Progressive concentrations of target molecule bronopol were then added to generate conformational change in the aptamer (which was preselected as an aptamer binding to bronopol from SEQ ID Nos. 189-301 flanked at its 5'-end with SEQ ID No. 304 and at its 3'-end with SEQ ID No. 305) to cause dehybridization or otherwise spacing from the indicator to decrease quenching and increase emitted signal due to excitation from the signal emitting label on the aptamer. FIG. 8 illustrates the fluorescence detected (shown at 560 nm from a 530 nm excitation source) at concentrations ranging from 0 to 200 ppm. As illustrated, a concentration-dependent increase in fluorescence was observed with increasing concentrations of the target bronopol.

Although the invention has been described with respect to specific embodiments thereof, these embodiments are merely illustrative, and not restrictive of the invention. The description herein of illustrated embodiments of the invention, including the description in the Abstract and Summary, is not intended to be exhaustive or to limit the invention to the precise forms disclosed herein (and in particular, the inclusion of any particular embodiment, feature or function within the Abstract or Summary is not intended to limit the scope of the invention to such embodiment, feature or function). Rather, the description is intended to describe illustrative embodiments, features and functions in order to provide a person of ordinary skill in the art context to understand the invention without limiting the invention to any particularly described embodiment, feature or function, including any such embodiment feature or function described in the Abstract or Summary. While specific embodiments of, and examples for, the invention are described herein for illustrative purposes only, various equivalent modifications are possible within the spirit and scope of the invention, as those skilled in the relevant art will recognize and appreciate. As indicated, these modifications may be made to the invention in light of the foregoing description of illustrated embodiments of the invention and are to be included within the spirit and scope of the invention. Thus, while the invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the invention.

Reference throughout this specification to "one embodiment", "an embodiment", or "a specific embodiment" or similar terminology means that a particular feature, structure, or characteristic described in connection with the embodiment is included in at least one embodiment and may not necessarily be present in all embodiments. Thus, respective appearances of the phrases "in one embodiment", "in an embodiment", or "in a specific embodiment" or similar terminology in various places throughout this specification are not necessarily referring to the same embodiment. Furthermore, the particular features, structures, or characteristics of any particular embodiment may be combined in any suitable manner with one or more other embodiments. It is to be understood that other variations and modifications of the embodiments described and illustrated herein are possible in light of the teachings herein and are to be considered as part of the spirit and scope of the invention.

In the description herein, numerous specific details are provided, such as examples of components and/or methods, to provide a thorough understanding of embodiments of the invention. One skilled in the relevant art will recognize, however, that an embodiment may be able to be practiced without one or more of the specific details, or with other apparatus, systems, assemblies, methods, components, materials, parts, and/or the like. In other instances, well-known structures, components, systems, materials, or operations are not specifically shown or described in detail to avoid obscuring aspects of embodiments of the invention. While the invention may be illustrated by using a particular embodiment, this is not and does not limit the invention to any particular embodiment and a person of ordinary skill in the art will recognize that additional embodiments are readily understandable and are a part of this invention.

As used herein, the terms "comprises," "comprising," "includes," "including," "has," "having," or any other variation thereof, are intended to cover a non-exclusive inclusion. For example, a process, product, article, or apparatus that comprises a list of elements is not necessarily limited only those elements but may include other elements not expressly listed or inherent to such process, process, article, or apparatus.

Furthermore, the term "or" as used herein is generally intended to mean "and/or" unless otherwise indicated. For example, a condition A or B is satisfied by any one of the following: A is true (or present) and B is false (or not present), A is false (or not present) and B is true (or present), and both A and B are true (or present). As used herein, including the claims that follow, a term preceded by "a" or "an" (and "the" when antecedent basis is "a" or "an") includes both singular and plural of such term, unless clearly indicated within the claim otherwise (i.e., that the reference "a" or "an" clearly indicates only the singular or only the plural). Also, as used in the description herein, the meaning of "in" includes "in" and "on" unless the context clearly dictates otherwise.

The invention claimed is:

1. A method for utilizing a nucleic acid array comprising:
providing a substrate with a plurality of single-stranded nucleic acid ligands located and attached at predetermined addresses on said substrate, each of said single-stranded nucleic acid ligands being an aptamer binding to a known target molecule with an identical hybridization sequence for each of said single-stranded nucleic acid ligands at one of said predetermined addresses, and forming a hybridization to a single-stranded nucleic acid label, each comprising a complementary hybridization sequence to said hybridization sequence;
incubating said substrate with a sample which may potentially contain at least one target molecule which binds to at least one of said plurality of single-stranded nucleic acid ligands; and
determining if any changes in said hybridizations occur after said incubating by performing a detection operation to detect potential changes in said hybridizations between said single-stranded nucleic acid labels and said single-stranded nucleic acid ligands correlated to said addresses;
wherein said potential changes in said hybridizations indicate binding of said at least one target molecule to at least one of said plurality of single-stranded nucleic acid ligands when a change in said hybridization occurs after adding said sample and no change in said hybridization after adding said sample indicates no binding of said at least one target molecule to any of said plurality of single-stranded nucleic acid ligands.

2. The method of claim 1, wherein said single-stranded nucleic acid ligands are selected for potential conformational changes upon binding to at least one of said target molecules.

3. The method of claim 1, wherein each of said hybridizations of said single-stranded nucleic acid ligands and said single-stranded nucleic acid labels comprise a signal interacting pair.

4. The method of claim 1, wherein each of said hybridizations of said single-stranded nucleic acid ligands and said single-stranded nucleic acid labels comprise a radiation-emitting label:radiation-modulating proximity interacting pair.

5. The method of claim 1, wherein said single-stranded nucleic acid ligands are attached to said substrate by covalent attachment.

6. The method of claim 1, wherein said single-stranded nucleic acid ligands are attached to said substrate by biotin coupling to streptavidin or similar molecules.

7. The method of claim 1, wherein said single-stranded nucleic acid ligands are attached to said substrate at a chosen distance to aid in reducing interference between adjacent single-stranded nucleic acid ligands.

8. The method of claim 1, wherein said potential changes are utilized to discriminate the relative binding affinity of said aptamers to said target molecule.

9. The method of claim 1, wherein said potential changes are utilized to determine a relative abundance of said target molecule in a sample.

10. The method of claim 1, wherein said single-stranded nucleic acid ligands include a spacing region between said substrate and a region that hybridizes to said single-stranded nucleic acid label.

11. The method of claim 10, wherein said spacing region is between 5 and 20 nucleotides in length.

12. The method of claim 1, wherein said at least one target molecule is selected from the group consisting of proteins, cells, small molecules and portions thereof.

13. The method of claim 1, wherein said substrate is selected from the group consisting of a multiwell plate, a collection of discrete droplets, labeled beads and coated glass.

14. The method of claim 1, wherein said single-stranded nucleic acid ligands comprise a target binding region between 22 and 42 nucleotides in length.

15. The method of claim 14, wherein said target binding region is a non-naturally occurring sequence.

16. The method of claim 1, wherein said detection operation is selected from the group consisting of microscopy, microscale thermophoresis (MST), and backscattering interferometry (BSI).

17. The method of claim 14, wherein said target binding region was selected by SELEX.

18. The method of claim 1, wherein said hybridization sequence is between 9 and 29 nucleotides in length.

* * * * *

SEQUENCE LISTING

<160> NUMBER OF SEQ ID NOS: 305

<210> SEQ ID NO 1
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 1
aaggcgtcga gaaatccagt tacactagga ca                                      32

<210> SEQ ID NO 2
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 2
aatagcagtg agaacttgac cgtcaacaca ta                                      32

<210> SEQ ID NO 3
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 3
aagttgagaa atccccacca tactaaggga aa                                      32

<210> SEQ ID NO 4
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 4

-continued aagttgagaa cttttaagaa aacagtcaca aa                                   32

<210> SEQ ID NO 5
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 5
aatgcagtga gaactttaaa accgtattaa ca                                   32

<210> SEQ ID NO 6
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 6
aattgagaac gctatgaaaa tagcacagtg cc                                   32

<210> SEQ ID NO 7
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 7
aattgagaaa tcccaacggt ccataaaagg ga                                   32

<210> SEQ ID NO 8
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 8
aattgagaac cctgataagg aaacagagca ct                                   32

<210> SEQ ID NO 9
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 9
aattgagaac gctttgatct cagacttagc tt                                   32

<210> SEQ ID NO 10
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 10
aattgagaac ttgaattaaa agtacatctc ac                                    32

<210> SEQ ID NO 11
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 11
aattgagaac tgtaagacca tgtaaactag ca                                    32

<210> SEQ ID NO 12
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 12
aattgagaac tgttgttagt caacccaagg at                                    32

<210> SEQ ID NO 13
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 13
aattgagaat gacgccaggg tgttacacag aa                                    32

<210> SEQ ID NO 14
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 14
aattgagaac tttccacaaa tgaaccagaa aa                                    32

<210> SEQ ID NO 15
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 15
aattgagaac tttgaaatca aatcagccac ta                                    32

<210> SEQ ID NO 16
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 16
aattgagaac tttttaccga tacatcataa ac                                    32

```
<210> SEQ ID NO 17
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 17
aattgaggac tctataatga tagcatatgc at                                    32

<210> SEQ ID NO 18
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 18
aattgaggac tctcacaatg agctaaggta ca                                    32

<210> SEQ ID NO 19
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 19
aaatcctaga atccatggag aactcttaaa ga                                    32

<210> SEQ ID NO 20
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 20
aagcagcagt gagaacgttt tactagaaaa cc                                    32

<210> SEQ ID NO 21
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 21
agggcagtga gaacgaaaat tttttatgcg ca                                    32

<210> SEQ ID NO 22
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 22
acaattgaga acgcttatcc atccaactaa ca                                    32
```

```
<210> SEQ ID NO 23
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 23
acattgagaa ctgtttttaa gaaccccgaa ga                                     32

<210> SEQ ID NO 24
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 24
acatgaagag gcgccaggac tcaggctgct ta                                     32

<210> SEQ ID NO 25
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 25
acggcagtga gaacgcaaaa ttcaaatatt aa                                     32

<210> SEQ ID NO 26
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 26
agatagcgtt gagaacgatg aacaatcagc tt                                     32

<210> SEQ ID NO 27
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 27
cacttatggc tcaagaggcg cggaagccgg ac                                     32

<210> SEQ ID NO 28
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 28
cagcaaacag agagccgcca gttgggaacg ta                                     32
```

```
<210> SEQ ID NO 29
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 29
caggctccgc tgcattgagg cgcgcaagat aa                                32

<210> SEQ ID NO 30
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 30
agttgagaac gctccctgga gtcaaaagat aa                                32

<210> SEQ ID NO 31
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 31
agttgagaac cctgtacttt aaacctctcc aa                                32

<210> SEQ ID NO 32
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 32
agttgagaac tttaagaaag gaatggctaa ca                                32

<210> SEQ ID NO 33
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 33
agttgagaac gtaagataat attacacgct aa                                32

<210> SEQ ID NO 34
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 34
agttgagagc gtagttagtt ctgtaaccga gg                                32

<210> SEQ ID NO 35
```

```
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 35
atcgcagtga gaacgtttga caaaacaaga aa                                       32

<210> SEQ ID NO 36
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 36
attgagaacg tcaaaattta cagttgatga ca                                       32

<210> SEQ ID NO 37
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 37
cagttgagaa cgtttacaaa acataaaatc ac                                       32

<210> SEQ ID NO 38
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 38
cagttgagaa cttattcaca catagccagc gc                                       32

<210> SEQ ID NO 39
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 39
ccacaagggc tggaggcgct gagagagtag ta                                       32

<210> SEQ ID NO 40
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 40
ccgcgtagcg gcagtgagga ctctcaatca gt                                       32

<210> SEQ ID NO 41
<211> LENGTH: 32
```

```
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 41
cgttgttcaa ccagttggga actctaccct tt                                  32

<210> SEQ ID NO 42
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 42
ctagcagtga gaatgacttt gaaaaatccg cc                                  32

<210> SEQ ID NO 43
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 43
ctagggcagt gaggactcat tttaagatgc ag                                  32

<210> SEQ ID NO 44
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 44
ctcgcgttga gaacgtttaa aaaactatat ca                                  32

<210> SEQ ID NO 45
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 45
ctgtagggct tcagaggcgc cgaacgccag ca                                  32

<210> SEQ ID NO 46
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 46
cttctgcatc tatcggcgtc aagctgactc gc                                  32

<210> SEQ ID NO 47
<211> LENGTH: 32
<212> TYPE: DNA
```

```
<213> ORGANISM: Artificial Sequence
<220> FEATURE:
<223> OTHER INFORMATION: Non-naturally occuring artificial aptamer
      sequence binding to a target molecule.

<400> SEQUENCE: 47
gaaaagccta gagattgagc gcagagaatg ac                                    32

<210> SEQ ID NO 48
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 48
gaagcaacga taccgcgcca cgacctcaag ca                                    32

<210> SEQ ID NO 49
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 49
gaatagtgat agcaaagagc atcgggaacg aa                                    32

<210> SEQ ID NO 50
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 50
gagttgagaa ctttcagtca ccgataaaca ta                                    32

<210> SEQ ID NO 51
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 51
gattatcacg ttgaaaggcg ctacaataga aa                                    32

<210> SEQ ID NO 52
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 52
gattcagagc agtgagaacg ccaaatttgt tc                                    32

<210> SEQ ID NO 53
<211> LENGTH: 32
<212> TYPE: DNA
<213> ORGANISM: Artificial Sequence
```

```
<220> FEATURE:
<223> OTHER INFORMATION: Non-naturally occuring artificial aptamer
      sequence binding to a target molecule.

<400> SEQUENCE: 53
gtattgcagc gagaacgtcg aaatatatga ca                                    32

<210> SEQ ID NO 54
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 54
gtcagcacac caggcgtctg aacggtcaag gc                                    32

<210> SEQ ID NO 55
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 55
gtcggccact taagccaagc agggagaatg ca                                    32

<210> SEQ ID NO 56
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 56
ggatacgcac gacgcgacgc aggccaacag ga                                    32

<210> SEQ ID NO 57
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 57
ggcacggtcg cagcgagaat ctccctaaaa ag                                    32

<210> SEQ ID NO 58
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 58
taggggcagt gagaacgcaa aaagaatag ac                                     32

<210> SEQ ID NO 59
<211> LENGTH: 32
<212> TYPE: DNA
<213> ORGANISM: Artificial Sequence
<220> FEATURE:
```

<223> OTHER INFORMATION: Non-naturally occuring artificial aptamer
      sequence binding to a target molecule.

<400> SEQUENCE: 59 tagggcagt gagaacgcaa ataggaatag ac                                      32

<210> SEQ ID NO 60
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 60
tagttgagaa cttgataaca ctgaacctaa aa                                     32

<210> SEQ ID NO 61
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 61
ttgcagggag aacttctata cttagactct gc                                     32

<210> SEQ ID NO 62
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 62
tcctgcagtg ggaacccccgt aatgttctta ca                                    32

<210> SEQ ID NO 63
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 63
tcctgcattg agaacccttta gtgagttatg aa                                    32

<210> SEQ ID NO 64
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 64
tgtggtgttg agaacgattc aaaatctgcc cc                                     32

<210> SEQ ID NO 65
<211> LENGTH: 32
<212> TYPE: DNA
<213> ORGANISM: Artificial Sequence
<220> FEATURE:
<223> OTHER INFORMATION: Non-naturally occuring artificial aptamer sequence binding to a target molecule.

<400> SEQUENCE: 65
ttgtcagaga gaacttcatt agacactaac cc					32

<210> SEQ ID NO 66
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 66
tttatgcgtt gacggcgata tcgttaagag gc					32

<210> SEQ ID NO 67
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 67
tttgagaact ttaccacgga acacgaaata ac					32

<210> SEQ ID NO 68
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 68
tttgagaact ttttacaaac gggcgggata ac					32

<210> SEQ ID NO 69
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 69
tttgagaatg gagaggttcg tcttaagtag tt					32

<210> SEQ ID NO 70
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 70
tcgaccgcgg acgtgggcgt agcagttggg tc					32

<210> SEQ ID NO 71
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

```
<400> SEQUENCE: 71
aggaactacg ctagctagac cagttcggat ta                                    32

<210> SEQ ID NO 72
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 72
agacatcgta ggtccagcca gttcgttctt at                                    32

<210> SEQ ID NO 73
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 73
ataactctgc ttatacgacc agttggtacc gg                                    32

<210> SEQ ID NO 74
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 74
agtcctatca ggcgtaatca gttactgtct tc                                    32

<210> SEQ ID NO 75
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 75
atgttagtta ggataatcag ttggtaggct cg                                    32

<210> SEQ ID NO 76
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 76
attagattcc tcttatcgcc agttgggcct tc                                    32

<210> SEQ ID NO 77
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.
```

<400> SEQUENCE: 77
attattttaa tccagttggg ttatccgtct cg                                32

<210> SEQ ID NO 78
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 78
caccccaggt tgatcagttg aagcgccttc cg                                32

<210> SEQ ID NO 79
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 79
caccgggcac ctgtggtggg ccagttcgac tt                                32

<210> SEQ ID NO 80
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 80
cacctggttg ggccagttgg gtgttacccc gc                                32

<210> SEQ ID NO 81
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 81
cactcaaaga atcagttgat agtctctgtt tc                                32

<210> SEQ ID NO 82
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 82
attgggcggg cccgcctcca gttgaacggc tt                                32

<210> SEQ ID NO 83
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 83
caaagctagg cgaagaattc cagttcgcgc gg                                32

<210> SEQ ID NO 84
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 84
caacagaacc ggttgggcag gccccgagct ta                                32

<210> SEQ ID NO 85
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 85
caataagatt gatcctgttg taatggttac cg                                32

<210> SEQ ID NO 86
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 86
catccagttg aaggcctgcc ggccgcgtcg cc                                32

<210> SEQ ID NO 87
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 87
catccagttg ttcatctcga ttctttccaa ga                                32

<210> SEQ ID NO 88
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 88
catctcgtat aagtgtaccc agttgtatct tc                                32

<210> SEQ ID NO 89
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 89

```
cactgggcat cgggtggacc ggtaagtctt aa                                32
```

```
<210> SEQ ID NO 90
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 90
cacttcggga tatcagttgt tcaccgtgat ct                                32
```

```
<210> SEQ ID NO 91
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 91
ccggcggcag cgctggagca gttgtggcct cg                                32
```

```
<210> SEQ ID NO 92
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 92
ccgggtctgg ctcccgggag cggttgattg ac                                32
```

```
<210> SEQ ID NO 93
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 93
ccgggttcgg ctcgactcgg gccagttgtg gc                                32
```

```
<210> SEQ ID NO 94
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 94
ccgggcggct gctcgaatcg gttgcgcggt ct                                32
```

```
<210> SEQ ID NO 95
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 95
ccatcgtggt aatcagttgt agctgtctac cg                                32
```

<210> SEQ ID NO 96
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 96
cccagaaggg gttacccagt tcgttttcac tg                                   32

<210> SEQ ID NO 97
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 97
ccccgcgcag tgtggccagt tgtaagtctc ga                                   32

<210> SEQ ID NO 98
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 98
ccccggttag gagggatcag ttcgcggcct cg                                   32

<210> SEQ ID NO 99
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 99
cccggcggtg gggaccagtt tgggtcgata ac                                   32

<210> SEQ ID NO 100
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 100
cccgtaagaa tcagttgtat cttcactgtt gc                                   32

<210> SEQ ID NO 101
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 101
ccttcggtaa gggccagttg gtaaatgtct tc                                   32

<210> SEQ ID NO 102
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 102
cgaagaagcg gttcttaaaa ttctcttgac tg                                      32

<210> SEQ ID NO 103
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 103
cgcgcgcacc gtgtgatcca gttcccgtcg gc                                      32

<210> SEQ ID NO 104
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 104
cgtgaatgtt caggcaggag ccagttcgga tt                                      32

<210> SEQ ID NO 105
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 105
cggatataaa gccaatccag ttgtagttct cg                                      32

<210> SEQ ID NO 106
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 106
cggccccagg cccagaagca gtttgcgacg gc                                      32

<210> SEQ ID NO 107
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 107
cggcggtcga cccggcggag cagttgactt gc                                      32

```
<210> SEQ ID NO 108
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 108
cgggcattgg accggcaccg gttgggtcgc ac                                   32

<210> SEQ ID NO 109
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 109
cggggtgtaa cgacgaagca gttccagtct ta                                   32

<210> SEQ ID NO 110
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 110
cgggtcagcg gccagttgga tgacagcctc gt                                   32

<210> SEQ ID NO 111
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 111
cggtcggtgg atcccggatc agttgttcgt cg                                   32

<210> SEQ ID NO 112
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 112
cggtctggcc gaaacggttg tcttcgcctt gc                                   32

<210> SEQ ID NO 113
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 113
cgtccacaat cagttcgtcg cgctcgctct gc                                   32

<210> SEQ ID NO 114
```

```
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 114
ctgagcaggg tctcaaagga aaccagttcg tc                                32

<210> SEQ ID NO 115
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 115
ctgcgcagtg tgaaccggtt gggaacggct cg                                32

<210> SEQ ID NO 116
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 116
ctcggctggc tcgggggcac caggaagcgt cg                                32

<210> SEQ ID NO 117
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 117
aaaataattt ataccagttg taatcattac cg                                32

<210> SEQ ID NO 118
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 118
aaactcgttt ataacagtta cagtcttcag tc                                32

<210> SEQ ID NO 119
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 119
aatgtagtac tagaccagtt gttcaccgga gc                                32

<210> SEQ ID NO 120
<211> LENGTH: 32
```

```
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 120
aattcggtat cggttatcca gttcggctcg gc                          32

<210> SEQ ID NO 121
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 121
actctgtgac cggttgttca ctggaatcga gg                          32

<210> SEQ ID NO 122
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 122
accctgttta acgggcaatc agttgtatct tc                          32

<210> SEQ ID NO 123
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 123
gaagcaccgc gacgaccagt tgggaccggt ga                          32

<210> SEQ ID NO 124
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 124
cttccctgaa gcagttgggc atgcgccccg tc                          32

<210> SEQ ID NO 125
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 125
cttgctcagc gggatactag ttgctcgttt ag                          32

<210> SEQ ID NO 126
<211> LENGTH: 32
<212> TYPE: DNA
```

```
<213> ORGANISM: Artificial Sequence
<220> FEATURE:
<223> OTHER INFORMATION: Non-naturally occuring artificial aptamer
      sequence binding to a target molecule.

<400> SEQUENCE: 126
gaaaatcagt tggcccttag ggaccggaag aa                                    32

<210> SEQ ID NO 127
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 127
gaaagcgtag tgatctcaat cagttgtatc tt                                    32

<210> SEQ ID NO 128
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 128
gacgggttta gcctcaaacc agttcggatt at                                    32

<210> SEQ ID NO 129
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 129
gagcggatgg ccgcgaaaac agttgggcct tc                                    32

<210> SEQ ID NO 130
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 130
gagggacggc cctcccggtt gcggtttaac gg                                    32

<210> SEQ ID NO 131
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 131
gcagaatcag ttcccgaagg gcgcggcgtc ta                                    32

<210> SEQ ID NO 132
<211> LENGTH: 32
<212> TYPE: DNA
<213> ORGANISM: Artificial Sequence
```

<220> FEATURE:
<223> OTHER INFORMATION: Non-naturally occuring artificial aptamer
      sequence binding to a target molecule.

<400> SEQUENCE: 132
gatcaggtcc ccgcagtccc agttgtcatc tt                                    32

<210> SEQ ID NO 133
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 133
gatcatgggc atcaatggtt gctagtcttc gc                                    32

<210> SEQ ID NO 134
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 134
ggcgtggcct gcctgttgtg tgcttcggac tg                                    32

<210> SEQ ID NO 135
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 135
ggaaatcaca ccagttgaaa gtactttccg ag                                    32

<210> SEQ ID NO 136
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 136
ggaaccttgg actccgaaca gttggcatct tc                                    32

<210> SEQ ID NO 137
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 137
ggacatccgg acaacaaagt tcgcggcggt ac                                    32

<210> SEQ ID NO 138
<211> LENGTH: 32
<212> TYPE: DNA
<213> ORGANISM: Artificial Sequence
<220> FEATURE:

```
<223> OTHER INFORMATION: Non-naturally occuring artificial aptamer
      sequence binding to a target molecule.

<400> SEQUENCE: 138
ggacgtaagt ctctccagtt gaaggttttc cg                                    32

<210> SEQ ID NO 139
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 139
ggagagaatc gataatcagt tgtcagcctt tg                                    32

<210> SEQ ID NO 140
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 140
ggcacaagtc agttgggttc tcgcagccgg cg                                    32

<210> SEQ ID NO 141
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 141
ggcagcaggg ctggttatca gttgtcatct cg                                    32

<210> SEQ ID NO 142
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 142
ggggtcaaca ggaccgcggg cagttcggat tc                                    32

<210> SEQ ID NO 143
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 143
gggtaccggc cagttcggcg gccgctggcg ac                                    32

<210> SEQ ID NO 144
<211> LENGTH: 32
<212> TYPE: DNA
<213> ORGANISM: Artificial Sequence
<220> FEATURE:
<223> OTHER INFORMATION: Non-naturally occuring artificial aptamer
``` sequence binding to a target molecule.

<400> SEQUENCE: 144
gggtcgcacg tggcccacta gttcggctcg gc                32

<210> SEQ ID NO 145
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 145
ggctccctga gcagcaattc agttgtcggc gg                32

<210> SEQ ID NO 146
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 146
gggaccggac ggtatcagtc agttgtcgcc gg                32

<210> SEQ ID NO 147
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 147
gggagagcaa atcccaccgg ttgtgttatt cg                32

<210> SEQ ID NO 148
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 148
gggcacaggc ttgggggctc accggttcgt cg                32

<210> SEQ ID NO 149
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 149
gggcagtggc tcagcggttg cggcgttagc tg                32

<210> SEQ ID NO 150
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 150
gggcattatg gtccatcagt tggaagctcc cg                                    32

<210> SEQ ID NO 151
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 151
ggtgtatcag atttctaacc agttggtacc gg                                    32

<210> SEQ ID NO 152
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 152
gggtgaggtg tcacgcaagt cagttgtctc tt                                    32

<210> SEQ ID NO 153
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 153
ggtaaagcag ttgtttcata gttcgtcttc at                                    32

<210> SEQ ID NO 154
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 154
ggtcccggat catcctgttg gcaccgcccg ag                                    32

<210> SEQ ID NO 155
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 155
ggtctcagtt ttgagtaatc agttgtctct tc                                    32

<210> SEQ ID NO 156
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 156
ggtgaaggcg acctgttggc ctggttggcc cg            32

<210> SEQ ID NO 157
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 157
ggtgaatatc gccgactagt tgcctcgcag aa            32

<210> SEQ ID NO 158
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 158
gtcccaccaa ctagttggcc ggctgcggcc cg            32

<210> SEQ ID NO 159
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 159
gtccggcggg agcgggcagc cggttgggcc tg            32

<210> SEQ ID NO 160
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 160
gtcgccagac tggccagttc gtgttacatt ag            32

<210> SEQ ID NO 161
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 161
gtactaacca gttcggatac acagtgcacg gc            32

<210> SEQ ID NO 162
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 162
gtagtcctaa acggaaaaca gttggcatct tc                                  32

<210> SEQ ID NO 163
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 163
gtcaatccag ttgggcccgc cccgagactg gg                                  32

<210> SEQ ID NO 164
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 164
gtcatctgag aaccggttga gcgctggctc cg                                  32

<210> SEQ ID NO 165
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 165
gtgtagcagc agttgttagt ctggcgtatt tg                                  32

<210> SEQ ID NO 166
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 166
taacgggcgg cacgatcgtt aggcagtgcg tc                                  32

<210> SEQ ID NO 167
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 167
taactggttt aaagtcagtt gtatgcttac cg                                  32

<210> SEQ ID NO 168
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 168
gtttcaattg agctaccagt tgtttgtcga ct            32

<210> SEQ ID NO 169
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 169
taaacgttca gttaagacca gttgtggcct cg            32

<210> SEQ ID NO 170
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 170
taatctaacg gagtggtacc agttgtcatc tt            32

<210> SEQ ID NO 171
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 171
taattttaga taataaatca gttgtcctct tc            32

<210> SEQ ID NO 172
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 172
tagggaccga ccccgcagac cagttggaac cg            32

<210> SEQ ID NO 173
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 173
tatcagttgt gggctgctat gtctaccggg ag            32

<210> SEQ ID NO 174
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 174
tatcatagat taccagttgt aacaccgagc tc            32

```
<210> SEQ ID NO 175
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 175
tcacgcaggt gatggaccag ttcgttcggt tg                                      32

<210> SEQ ID NO 176
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 176
tcagaatagc taaccggttg caggctaacg ac                                      32

<210> SEQ ID NO 177
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 177
tccagttggg atttattgcc ggaagcaccg tt                                      32

<210> SEQ ID NO 178
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 178
tcccggtctg accgaaagcc agttggcacc gg                                      32

<210> SEQ ID NO 179
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 179
tgaggttccc cgtcggacca gttggttgaa gg                                      32

<210> SEQ ID NO 180
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 180
tctctcggca gatagcagtt gtttcatctt gg                                      32
```

<210> SEQ ID NO 181
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 181
tcttaggaag cagttgggcg aaaagtgtcg tg                                32

<210> SEQ ID NO 182
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 182
tgctgtatgg ccatatccag ttgtatttac cg                                32

<210> SEQ ID NO 183
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 183
tggcacgaaa tcagttcgcg gactgctgtc ct                                32

<210> SEQ ID NO 184
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 184
tgtggtaaca atatcagttg ttagtctatg tg                                32

<210> SEQ ID NO 185
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 185
tgtgcgtttg cgcgctccag ttgttagtat cg                                32

<210> SEQ ID NO 186
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 186
ttccagttgt atttaaccga tagttctatt ga                                32

```
<210> SEQ ID NO 187
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 187
ttccagttgt tcacggctca cgcggaaccg ag                                    32

<210> SEQ ID NO 188
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 188
ttgtgggcaa atacagttgg tggcctctcc cg                                    32

<210> SEQ ID NO 189
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 189
agcttctgag atatccagtt gtttagtctc ga                                    32

<210> SEQ ID NO 190
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 190
aggcacccct gaccagttgg gcacccgaag gt                                    32

<210> SEQ ID NO 191
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 191
aggctttacc agttgtgaat ttatttttgc tg                                    32

<210> SEQ ID NO 192
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 192
agattctaat cagttgtgta atagttgtgt gt                                    32

<210> SEQ ID NO 193
```

```
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 193
agcctaaatt taggagaatc agttcgtttt ag                                    32

<210> SEQ ID NO 194
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 194
agcgagacct tgctccagtt gttcaccgta gt                                    32

<210> SEQ ID NO 195
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 195
agcgtaagcg taggcagttg ttcctagtct cg                                    32

<210> SEQ ID NO 196
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 196
ataacttcaa gtgtatttcc agttgtatct ta                                    32

<210> SEQ ID NO 197
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 197
ataagcagtt gtaccagttg aaagcctttc cg                                    32

<210> SEQ ID NO 198
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 198
agggaatgat aattagctaa gcagttgtag tc                                    32

<210> SEQ ID NO 199
<211> LENGTH: 32
```

```
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 199
aggtattaca tacgttacca gttgggaccg gt                                32

<210> SEQ ID NO 200
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 200
aggtttataa cataccagtt ggaaggctcc cg                                32

<210> SEQ ID NO 201
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 201
agtgagacta tcactgatca gttgggatta ac                                32

<210> SEQ ID NO 202
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 202
atagtttcct ttaccagttc gtattcactg ct                                32

<210> SEQ ID NO 203
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 203
cacgagacct cgcgatatca gttgggcctt ag                                32

<210> SEQ ID NO 204
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 204
attgtttcaa tgaccggttg gtattcccga gt                                32

<210> SEQ ID NO 205
<211> LENGTH: 32
<212> TYPE: DNA
```

<213> ORGANISM: Artificial Sequence
<220> FEATURE:
<223> OTHER INFORMATION: Non-naturally occuring artificial aptamer
    sequence binding to a target molecule.

<400> SEQUENCE: 205
atttgtttca cgagtaatca gttgtccatt tg        32

<210> SEQ ID NO 206
<211> LENGTH: 32
<212> TYPE: DNA
<213> ORGANISM: Artificial Sequence
<220> FEATURE:
<223> OTHER INFORMATION: Non-naturally occuring artificial aptamer
    sequence binding to a target molecule.

<400> SEQUENCE: 206
cacagaatgt tggatcagtt gttaggatta tg        32

<210> SEQ ID NO 207
<211> LENGTH: 32
<212> TYPE: DNA
<213> ORGANISM: Artificial Sequence
<220> FEATURE:
<223> OTHER INFORMATION: Non-naturally occuring artificial aptamer
    sequence binding to a target molecule.

<400> SEQUENCE: 207
catattatgc tttccagttg acagtctcga tt        32

<210> SEQ ID NO 208
<211> LENGTH: 32
<212> TYPE: DNA
<213> ORGANISM: Artificial Sequence
<220> FEATURE:
<223> OTHER INFORMATION: Non-naturally occuring artificial aptamer
    sequence binding to a target molecule.

<400> SEQUENCE: 208
catattcgtc agaggaatca gttgttggat cg        32

<210> SEQ ID NO 209
<211> LENGTH: 32
<212> TYPE: DNA
<213> ORGANISM: Artificial Sequence
<220> FEATURE:
<223> OTHER INFORMATION: Non-naturally occuring artificial aptamer
    sequence binding to a target molecule.

<400> SEQUENCE: 209
catatttgga ccagttgtag ttgtgcagtg at        32

<210> SEQ ID NO 210
<211> LENGTH: 32
<212> TYPE: DNA
<213> ORGANISM: Artificial Sequence
<220> FEATURE:
<223> OTHER INFORMATION: Non-naturally occuring artificial aptamer
    sequence binding to a target molecule.

<400> SEQUENCE: 210
cagcttagga atcagttggt atttcccgag ta        32

<210> SEQ ID NO 211
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 211
cagtaaatgt ctttatacca gttgaagtct aa                                       32

<210> SEQ ID NO 212
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 212
cagtctagtg aatccagttg atgggctatc cg                                       32

<210> SEQ ID NO 213
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 213
cagttaagaa gcagttgtca tttgctgacc ga                                       32

<210> SEQ ID NO 214
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 214
cagtggaaca ggagccagtt gattgctatc cg                                       32

<210> SEQ ID NO 215
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 215
ccggcggcag gctggacacc ggttgcccgc tg                                       32

<210> SEQ ID NO 216
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 216
ccgacagagg aggtaatcag ttgtcatctt aa                                       32

<210> SEQ ID NO 217
<211> LENGTH: 32
<212> TYPE: DNA
<213> ORGANISM: Artificial Sequence
<220> FEATURE:

<223> OTHER INFORMATION: Non-naturally occuring artificial aptamer
      sequence binding to a target molecule.

<400> SEQUENCE: 217
cgcgggtggt aattcacgct aagcagttcg tc                                32

<210> SEQ ID NO 218
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 218
cgctgtaaca gcgggccagt tcggattaat tt                                32

<210> SEQ ID NO 219
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 219
cgactgtggg cgaagcagtt gttggctctg tg                                32

<210> SEQ ID NO 220
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 220
cgcaaagaag cagttggaaa agtctcggcg gt                                32

<210> SEQ ID NO 221
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 221
cggatagaat tagaaacagt tggtaaccga gc                                32

<210> SEQ ID NO 222
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 222
cggcagggaa tcgccggacc ggttggcacc gg                                32

<210> SEQ ID NO 223
<211> LENGTH: 32
<212> TYPE: DNA
<213> ORGANISM: Artificial Sequence
<220> FEATURE:
<223> OTHER INFORMATION: Non-naturally occuring artificial aptamer sequence binding to a target molecule.

<400> SEQUENCE: 223
cggggtttct ccggccagtt gtggaaccga gt          32

<210> SEQ ID NO 224
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 224
ctctgaaccg gttgtgaata ttcgttgatc tg          32

<210> SEQ ID NO 225
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 225
ctgcaagagc cagttgtgga atcaccgagc gc          32

<210> SEQ ID NO 226
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 226
ctaacggagt gtgacctgtt gtaagtttac cg          32

<210> SEQ ID NO 227
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 227
ctaagacata tgtctaataa tcagtgcgtg tt          32

<210> SEQ ID NO 228
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 228
ctataagaat cagttgggta aggatgaatc ga          32

<210> SEQ ID NO 229
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

```
<400> SEQUENCE: 229
ctctagttct ctgaggttca gtttctgtct tc                                    32

<210> SEQ ID NO 230
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 230
aaaatttaaa cagttggttt cacccgtagg gt                                    32

<210> SEQ ID NO 231
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 231
aacgtagtgg agaccagttg tttagaccga gt                                    32

<210> SEQ ID NO 232
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 232
aattaattaa gcagttggta ggcttctctt gc                                    32

<210> SEQ ID NO 233
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 233
acagaaacag tatctgtaaa cagttgggtt ag                                    32

<210> SEQ ID NO 234
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 234
aaggtagatt aaccggttgt tagtcctatt tg                                    32

<210> SEQ ID NO 235
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.
```

<400> SEQUENCE: 235
cttaagcagt tggatttatt ctcgagtagt tt 32

<210> SEQ ID NO 236
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 236
cttaatggaa acagttgtag cgttagtgcc gt 32

<210> SEQ ID NO 237
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 237
cttgtgcgcg cactagaatc ggttgtatct tc 32

<210> SEQ ID NO 238
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 238
ctttagaggc agttgttcgg caagaaccgg ga 32

<210> SEQ ID NO 239
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 239
gaacttcgag gtcaaaacag ttcggattca ct 32

<210> SEQ ID NO 240
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 240
gagtagccct gctaggatcc agttgtatct tc 32

<210> SEQ ID NO 241
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 241

```
gactcttggt aaatcagttc gttctttcag gt                                    32
```

<210> SEQ ID NO 242
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 242

```
gagaatttga ccagttgtga aggccctcac cg                                    32
```

<210> SEQ ID NO 243
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 243

```
gataaatcag ttgggaactt aggcttggcg tg                                    32
```

<210> SEQ ID NO 244
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 244

```
gataaatcca gttgttattc aaaccgaagt gt                                    32
```

<210> SEQ ID NO 245
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 245

```
gattcgggca tgtcataatt aaacagttcg tc                                    32
```

<210> SEQ ID NO 246
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 246

```
gatttgctaa tcctttccag ttggtaggct cg                                    32
```

<210> SEQ ID NO 247
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 247
gcacgcggag cttgcgaccg gttcgcgcgg gt                                        32

<210> SEQ ID NO 248
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 248
gccctcagta aacagttgga aatggcttcc cg                                        32

<210> SEQ ID NO 249
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 249
ggaaagcagt tgttataata tcgtctgtac gg                                        32

<210> SEQ ID NO 250
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 250
ggaggcaaat ccaactagtt gtaggcatac cg                                        32

<210> SEQ ID NO 251
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 251
ggcacaaaca gttgggaccg aggtcgatca gc                                        32

<210> SEQ ID NO 252
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 252
ggcaccggca cggcgaccgg ccagttcgtt cg                                        32

<210> SEQ ID NO 253
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 253
ggcattgttt aaggtctaat cagtttgtct tc                                        32

```
<210> SEQ ID NO 254
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 254
gggtccgccc ggccagttgt cgccctgctt gc                                    32

<210> SEQ ID NO 255
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 255
gggcagcagg caccaaacag ttggtaaccg ag                                    32

<210> SEQ ID NO 256
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 256
gggttaacaa tcagttggtt tcccggaggt tt                                    32

<210> SEQ ID NO 257
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 257
ggtaatatat agtcacaagc agttgtatct ta                                    32

<210> SEQ ID NO 258
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 258
gtccagttaa tctagcgacc agttgggctt tc                                    32

<210> SEQ ID NO 259
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 259
gtaaaacagt tggatcggta tcccgagaag gt                                    32
```

<210> SEQ ID NO 260
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 260
ggttttagca atcagttgtt cgcctttgct ct                                     32

<210> SEQ ID NO 261
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 261
gtactaaaca gttgttcggc ttatgaagag aa                                     32

<210> SEQ ID NO 262
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 262
gtagtcctgt acggtaccag ttgggtaatt ag                                     32

<210> SEQ ID NO 263
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 263
gtagtggcaa tcagttgtga ttcgaagaat tg                                     32

<210> SEQ ID NO 264
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 264
gtatggttga tcctacaggc agttcagtct tc                                     32

<210> SEQ ID NO 265
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 265
gtgaatctat ggaagaccag ttgtcggcct cg                                     32

```
<210> SEQ ID NO 266
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 266
gtggtaggca agcagttgtg caggcaccga at                                       32

<210> SEQ ID NO 267
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 267
gtgtaacaga ccagttcata ttcattgcgt cg                                       32

<210> SEQ ID NO 268
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 268
taacgttttc tatttaatcc agttgtatct tc                                       32

<210> SEQ ID NO 269
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 269
taactctagt aagtaccagt tgatttcatc cg                                       32

<210> SEQ ID NO 270
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 270
taagcgttta aatcagttgg attgctgtcc cg                                       32

<210> SEQ ID NO 271
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 271
tagagtgatt ctcctcgtta ccagttcggc ta                                       32

<210> SEQ ID NO 272
```

```
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 272
tagccttgca taatcagttg tcttcttagt gc                                   32

<210> SEQ ID NO 273
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 273
tagcgcttca ggattaatca gttgtcatct tc                                   32

<210> SEQ ID NO 274
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 274
tagctctaaa tcagttcgta ttaacttgga ag                                   32

<210> SEQ ID NO 275
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 275
tatatcgtta tgtaaccagt tgttagtggt ag                                   32

<210> SEQ ID NO 276
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 276
tatccagttc gttattaacg cgaggaagtt tg                                   32

<210> SEQ ID NO 277
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 277
tatccagtta gtttagcgtg cgtcgccgca tt                                   32

<210> SEQ ID NO 278
<211> LENGTH: 32
```

```
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 278
tcgcacgtac tgtgggagcc agttggtacc gg                              32

<210> SEQ ID NO 279
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 279
tcagaaagga aagcagttga tcagtctttc ga                              32

<210> SEQ ID NO 280
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 280
tcagaaaggt ctgtgaccag ttgtagtcct cg                              32

<210> SEQ ID NO 281
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 281
tcatccagtt gtgaagtctc gataagtgtc tt                              32

<210> SEQ ID NO 282
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 282
tccgcaggtt ccagttgttt ccaccgagtg gc                              32

<210> SEQ ID NO 283
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 283
tgaccagttg tttaatgtaa ttcgtctcat gg                              32

<210> SEQ ID NO 284
<211> LENGTH: 32
<212> TYPE: DNA
```

```
<213> ORGANISM: Artificial Sequence
<220> FEATURE:
<223> OTHER INFORMATION: Non-naturally occuring artificial aptamer
      sequence binding to a target molecule.

<400> SEQUENCE: 284
tctaaacagt tggtatgggt acataaccga ga                                     32

<210> SEQ ID NO 285
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 285
tctcagtgaa atcagttgtt ttaatcggct cg                                     32

<210> SEQ ID NO 286
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 286
tctggtacgg aaagcagttg ggcctggtac gg                                     32

<210> SEQ ID NO 287
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 287
tctttggcca aaaagccagt tgtattaacc ga                                     32

<210> SEQ ID NO 288
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 288
tgatgagtca aactagttgt atttgtcgct gc                                     32

<210> SEQ ID NO 289
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 289
tgattgctag aaataaccag ttgttagtaa ag                                     32

<210> SEQ ID NO 290
<211> LENGTH: 32
<212> TYPE: DNA
<213> ORGANISM: Artificial Sequence
```

```
<220> FEATURE:
<223> OTHER INFORMATION: Non-naturally occuring artificial aptamer
      sequence binding to a target molecule.

<400> SEQUENCE: 290
tgcgaagtaa attccagttg gtaaccaccc ga                                   32

<210> SEQ ID NO 291
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 291
tgggtatgtc cataagcagt tgggaccggt gt                                   32

<210> SEQ ID NO 292
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 292
tggagctgta gcgcaatgac cagttcgtat ta                                   32

<210> SEQ ID NO 293
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 293
tgtgtgaacg ttaatccagt tgtttgttac cg                                   32

<210> SEQ ID NO 294
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 294
tgtaaagcag ttgtagccag gctaaccgag at                                   32

<210> SEQ ID NO 295
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 295
tgtgcatcat accagttgtt gaattaccga gt                                   32

<210> SEQ ID NO 296
<211> LENGTH: 32
<212> TYPE: DNA
<213> ORGANISM: Artificial Sequence
<220> FEATURE:
```

```
<223> OTHER INFORMATION: Non-naturally occuring artificial aptamer
      sequence binding to a target molecule.

<400> SEQUENCE: 296
ttccagttcg ttcattttcc ataagctttg ac                                    32

<210> SEQ ID NO 297
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 297
tgttaaaagc agttgttagt cggagacggt gt                                    32

<210> SEQ ID NO 298
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 298
tgttacaagg cagttgttta gctcgtctcg gc                                    32

<210> SEQ ID NO 299
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 299
tgttatacgt agtatccagt ttgctagtct gc                                    32

<210> SEQ ID NO 300
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 300
tgttgcacat ggctcagacc agttgtttac cg                                    32

<210> SEQ ID NO 301
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 301
ttgtaagtac ttaatcagtt ggggctcgat tg                                    32

<210> SEQ ID NO 302
<211> LENGTH: 19
<212> TYPE: DNA
<213> ORGANISM: Artificial Sequence
<220> FEATURE:
<223> OTHER INFORMATION: Artificial, non-naturally occuring 5' primer
```

```
            sequence

<400> SEQUENCE: 302
gcgccggagt tctcaatgc                                               19

<210> SEQ ID NO 303
<211> LENGTH: 19
<212> TYPE: DNA
<213> ORGANISM: Artificial Sequence
<220> FEATURE:
<223> OTHER INFORMATION: Artificial, non-naturally occuring 3' primer
            sequence

<400> SEQUENCE: 303
gcatgccggt cggtctact                                               19

<210> SEQ ID NO 304
<211> LENGTH: 19
<212> TYPE: DNA
<213> ORGANISM: Artificial Sequence
<220> FEATURE:
<223> OTHER INFORMATION: Artificial, non-naturally occuring 5' primer
            sequence

<400> SEQUENCE: 304
tgtcaagacg caactggtt                                               19

<210> SEQ ID NO 305
<211> LENGTH: 19
<212> TYPE: DNA
<213> ORGANISM: Artificial Sequence
<220> FEATURE:
<223> OTHER INFORMATION: Artificial, non-naturally occuring 3' primer
            sequence

<400> SEQUENCE: 305
actctcggca tcgtaggca                                               19
```